(12) United States Patent
Kramer

(10) Patent No.: US 7,201,940 B1
(45) Date of Patent: Apr. 10, 2007

(54) METHOD AND APPARATUS FOR THERMAL SPRAY PROCESSING OF MEDICAL DEVICES

(75) Inventor: Pamela A. Kramer, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 528 days.

(21) Appl. No.: 09/880,514

(22) Filed: Jun. 12, 2001

(51) Int. Cl.
B05D 1/02 (2006.01)

(52) U.S. Cl. .................. 427/189; 427/191; 427/202; 427/205; 427/427

(58) Field of Classification Search .............. 427/189, 427/191, 192, 199, 202, 205, 294–296, 427
See application file for complete search history.

(56) References Cited

U.S. PATENT DOCUMENTS

| | | | |
|---|---|---|---|
| 3,105,492 A | 10/1963 | Jeckel | 128/334 |
| 3,288,728 A | 11/1966 | Gorham | 260/2 |
| 3,657,744 A | 4/1972 | Ersek | 3/1 |
| 3,839,743 A | 10/1974 | Schwarc | 3/1 |
| 3,993,078 A | 11/1976 | Bergentz et al. | 128/334 R |
| 4,130,904 A | 12/1978 | Whalen | 3/1.4 |
| 4,140,126 A | 2/1979 | Choudhury | 128/325 |
| 4,159,719 A | 7/1979 | Haer | 128/260 |
| 4,346,028 A | 8/1982 | Griffith | 524/417 |
| 4,411,055 A | 10/1983 | Simpson et al. | 29/447 |
| 4,503,569 A | 3/1985 | Dotter | 3/1.4 |
| 4,512,338 A | 4/1985 | Balko et al. | 128/1 R |
| 4,531,933 A | 7/1985 | Norton et al. | 604/8 |
| 4,553,545 A | 11/1985 | Maass et al. | 128/341 |
| 4,580,568 A | 4/1986 | Gianturco | 128/345 |
| 4,604,762 A | 8/1986 | Robinson | 623/1 |
| 4,619,246 A | 10/1986 | Molgaard-Nielsen et al. | 128/1 R |

(Continued)

FOREIGN PATENT DOCUMENTS

CA 2008312 7/1990

(Continued)

OTHER PUBLICATIONS

Donadille, C., et al.; "Overview No. 82—Development of Texture and Microstructure During Cold-Rolling and Annealing of F.C.C. Alloys: Example of an Austenitic Stainless Steel," *Acta metall.*, vol. 37, No. 6, 1989, pp. 1547-1571.

(Continued)

Primary Examiner—Michael Miggins
(74) Attorney, Agent, or Firm—Squire, Sanders & Dempsey L.L.P.

(57) ABSTRACT

The invention relates to devices for the treatment of heart disease and particularly to endo-arterial prostheses, which are commonly called stents. More particularly, the invention relates to methods of manufacturing and coating stents utilizing thermal spray processing (TSP). In one aspect the invention involves the use of TSP for the manufacture of fine grained tubing for subsequent use as a stent or other tubular or ring-based implant, or the manufacture of intermediate sized tubing that may then be drawn to final size tubing and for the coating of a stent. An average grain size of less than 64 microns is achieved by the invention resulting in a stent having an annular wall average thickness of about eight or more grains.

16 Claims, 7 Drawing Sheets

U.S. PATENT DOCUMENTS

| | | | |
|---|---|---|---|
| 4,633,873 A | 1/1987 | Dumican et al. | 128/334 R |
| 4,649,922 A | 3/1987 | Wiktor | 128/344 |
| 4,650,466 A | 3/1987 | Luther | 604/95 |
| 4,655,771 A | 4/1987 | Wallsten | 623/1 |
| 4,656,083 A | 4/1987 | Hoffman et al. | 428/265 |
| 4,681,110 A | 7/1987 | Wiktor | 128/343 |
| 4,681,734 A * | 7/1987 | Simm et al. | 419/9 |
| 4,699,611 A | 10/1987 | Bowden | 604/51 |
| 4,706,671 A | 11/1987 | Weinrib | 128/348.1 |
| 4,718,907 A | 1/1988 | Karwoski et al. | 623/12 |
| 4,722,335 A | 2/1988 | Vilasi | 128/207.14 |
| 4,723,549 A | 2/1988 | Wholey et al. | 128/344 |
| 4,728,328 A | 3/1988 | Hughes et al. | 623/12 |
| 4,739,762 A | 4/1988 | Palmaz | 128/343 |
| 4,740,207 A | 4/1988 | Kreamer | 623/1 |
| 4,762,128 A | 8/1988 | Rosenbluth | 128/343 |
| 4,776,337 A | 10/1988 | Palmaz | 128/343 |
| 4,800,882 A | 1/1989 | Gianturco | 128/343 |
| 4,816,339 A | 3/1989 | Tu et al. | 428/421 |
| 4,848,343 A | 7/1989 | Wallstén et al. | 128/343 |
| 4,856,516 A | 8/1989 | Hillstead | 128/343 |
| 4,870,966 A | 10/1989 | Dellon et al. | 128/334 R |
| 4,877,030 A | 10/1989 | Beck et al. | 128/343 |
| 4,878,906 A | 11/1989 | Lindemann et al. | 623/1 |
| 4,879,135 A | 11/1989 | Greco et al. | 427/2 |
| 4,886,062 A | 12/1989 | Wiktor | 128/343 |
| 4,892,539 A | 1/1990 | Koch | 623/1 |
| 4,893,623 A | 1/1990 | Rosenbluth | 606/192 |
| 4,907,336 A | 3/1990 | Gianturco | 29/515 |
| 4,913,141 A | 4/1990 | Hillstead | 606/108 |
| 4,922,905 A | 5/1990 | Strecker | 606/195 |
| 4,943,346 A | 7/1990 | Mattelin | 156/651 |
| 4,950,227 A | 8/1990 | Savis et al. | 604/8 |
| 4,969,458 A | 11/1990 | Wiktor | 606/194 |
| 4,969,890 A | 11/1990 | Sugita et al. | 606/192 |
| 4,981,478 A | 1/1991 | Evard et al. | 604/282 |
| 4,986,831 A | 1/1991 | King et al. | 623/1 |
| 4,990,155 A | 2/1991 | Wilkoff | 606/191 |
| 4,994,071 A | 2/1991 | MacGregor | 606/194 |
| 4,994,298 A | 2/1991 | Yasuda | 427/41 |
| 4,998,539 A | 3/1991 | Delsanti | 128/898 |
| 5,002,560 A | 3/1991 | Machold et al. | 606/198 |
| 5,007,926 A | 4/1991 | Derbyshire | 623/1 |
| 5,015,253 A | 5/1991 | MacGregor | 623/1 |
| 5,019,085 A | 5/1991 | Hillstead | 606/108 |
| 5,026,377 A | 6/1991 | Burton et al. | 606/108 |
| 5,034,001 A | 7/1991 | Garrison et al. | 604/53 |
| 5,035,706 A | 7/1991 | Gianturco et al. | 606/194 |
| 5,037,377 A | 8/1991 | Alonso | 600/36 |
| 5,037,392 A | 8/1991 | Hillstead | 604/96 |
| 5,037,427 A | 8/1991 | Harada et al. | 606/108 |
| 5,041,126 A | 8/1991 | Gianturco | 606/195 |
| 5,047,050 A | 9/1991 | Arpesani | 623/1 |
| 5,053,048 A | 10/1991 | Pinchuk | 623/1 |
| 5,059,211 A | 10/1991 | Stack et al. | 606/198 |
| 5,061,275 A | 10/1991 | Wallstén et al. | 623/1 |
| 5,062,829 A | 11/1991 | Pryor et al. | 604/57 |
| 5,064,435 A | 11/1991 | Porter | 623/12 |
| 5,071,407 A | 12/1991 | Termin et al. | 604/104 |
| 5,078,720 A | 1/1992 | Burton et al. | 606/108 |
| 5,078,726 A | 1/1992 | Kreamer | 606/194 |
| 5,078,736 A | 1/1992 | Behl | 623/1 |
| 5,084,065 A | 1/1992 | Weldon et al. | 623/1 |
| 5,085,629 A | 2/1992 | Goldberg et al. | 604/8 |
| 5,089,005 A | 2/1992 | Harada | 606/194 |
| 5,092,877 A | 3/1992 | Pinchuk | 623/1 |
| 5,100,429 A | 3/1992 | Sinofsky et al. | 606/195 |
| 5,102,417 A | 4/1992 | Palmaz | 606/195 |
| 5,107,852 A | 4/1992 | Davidson et al. | 128/772 |
| 5,108,416 A | 4/1992 | Ryan et al. | 606/194 |
| 5,108,417 A | 4/1992 | Sawyer | 606/198 |
| 5,108,755 A | 4/1992 | Daniels et al. | 424/426 |
| 5,116,318 A | 5/1992 | Hillstead | 604/96 |
| 5,116,360 A | 5/1992 | Pinchuk et al. | 623/1 |
| 5,116,365 A | 5/1992 | Hillstead | 623/1 |
| 5,122,154 A | 6/1992 | Rhodes | 606/198 |
| 5,123,917 A | 6/1992 | Lee | 623/1 |
| 5,133,732 A | 7/1992 | Wiktor | 606/195 |
| 5,135,516 A | 8/1992 | Sahatjian et al. | 604/295 |
| 5,135,536 A | 8/1992 | Hillstead | 606/195 |
| 5,151,105 A | 9/1992 | Kwan-Gett | 623/1 |
| 5,156,623 A | 10/1992 | Hakamatsuka et al. | 623/11 |
| 5,161,547 A | 11/1992 | Tower | 128/898 |
| 5,163,958 A | 11/1992 | Pinchuk | 623/11 |
| 5,171,262 A | 12/1992 | MacGregor | 623/1 |
| 5,176,661 A | 1/1993 | Evard et al. | 604/282 |
| 5,183,085 A | 2/1993 | Timmermans | 140/89 |
| 5,192,297 A | 3/1993 | Hull | 606/195 |
| 5,192,307 A | 3/1993 | Wall | 623/1 |
| 5,192,311 A | 3/1993 | King et al. | 623/1 |
| 5,197,977 A | 3/1993 | Hoffman, Jr. et al. | 623/1 |
| 5,206,341 A | 4/1993 | Ibay et al. | 528/361 |
| 5,222,971 A | 6/1993 | Willard et al. | 606/158 |
| 5,226,913 A | 7/1993 | Pinchuk | 623/1 |
| 5,234,416 A | 8/1993 | Macaulay et al. | 604/282 |
| 5,234,456 A | 8/1993 | Silvestrini | 606/192 |
| 5,234,457 A | 8/1993 | Andersen | 606/198 |
| 5,236,447 A | 8/1993 | Kubo et al. | 623/1 |
| 5,269,802 A | 12/1993 | Garber | 606/191 |
| 5,279,594 A | 1/1994 | Jackson | 604/265 |
| 5,282,823 A | 2/1994 | Schwartz et al. | 606/198 |
| 5,282,860 A | 2/1994 | Matsuno et al. | 623/12 |
| 5,289,831 A | 3/1994 | Bosley | 128/899 |
| 5,290,230 A | 3/1994 | Ainsworth et al. | 604/96 |
| 5,290,271 A | 3/1994 | Jernberg | 604/891.1 |
| 5,302,414 A | 4/1994 | Alkhimov et al. | 427/192 |
| 5,304,200 A | 4/1994 | Spaulding | 606/198 |
| 5,306,286 A | 4/1994 | Stack et al. | 606/198 |
| 5,314,444 A | 5/1994 | Gianturco | 606/195 |
| 5,314,472 A | 5/1994 | Fontaine | 623/12 |
| 5,330,500 A | 7/1994 | Song | 606/198 |
| 5,342,348 A | 8/1994 | Kaplan | 604/891.1 |
| 5,342,621 A | 8/1994 | Eury | 424/423 |
| 5,356,433 A | 10/1994 | Rowland et al. | 623/11 |
| 5,358,533 A * | 10/1994 | Noiles et al. | 623/22 |
| 5,360,443 A | 11/1994 | Barone et al. | 623/1 |
| 5,364,354 A | 11/1994 | Walker et al. | 604/96 |
| 5,366,504 A | 11/1994 | Andersen et al. | 623/11 |
| 5,370,684 A | 12/1994 | Vallana et al. | 623/1 |
| 5,383,927 A | 1/1995 | De Goicoechea et al. | 623/1 |
| 5,389,106 A | 2/1995 | Tower | 606/198 |
| 5,415,546 A | 5/1995 | Cox, Sr. | 433/213 |
| 5,421,955 A | 6/1995 | Lau et al. | 216/48 |
| 5,423,849 A | 6/1995 | Engelson et al. | 606/191 |
| 5,423,885 A | 6/1995 | Williams | 623/1 |
| 5,449,373 A | 9/1995 | Pinchasik et al. | 606/198 |
| 5,451,209 A | 9/1995 | Ainsworth et al. | 604/96 |
| 5,464,650 A | 11/1995 | Berg et al. | 427/2.3 |
| 5,531,715 A | 7/1996 | Engelson et al. | 604/265 |
| 5,538,512 A | 7/1996 | Zenzon et al. | 604/280 |
| 5,562,621 A | 10/1996 | Claude et al. | 604/100 |
| 5,562,728 A | 10/1996 | Lazarus et al. | 623/1 |
| 5,569,295 A | 10/1996 | Lam | 606/198 |
| 5,571,166 A | 11/1996 | Dinh et al. | 623/1 |
| 5,601,538 A | 2/1997 | Deem | 604/280 |
| 5,601,593 A | 2/1997 | Freitag | 606/198 |
| 5,603,991 A | 2/1997 | Kupiecki et al. | 427/508 |
| 5,607,442 A | 3/1997 | Fischell et al. | 606/191 |
| 5,609,629 A | 3/1997 | Fearnot et al. | 623/1 |
| 5,618,298 A | 4/1997 | Simon | 606/194 |
| 5,624,411 A | 4/1997 | Tuch | 604/265 |
| 5,628,755 A | 5/1997 | Heller et al. | 606/108 |
| 5,628,781 A | 5/1997 | Williams et al. | 623/1 |
| 5,630,829 A | 5/1997 | Lauterjung | 606/198 |

| Patent No. | Date | Inventor | Class |
|---|---|---|---|
| 5,636,641 A | 6/1997 | Fariabi ................ 128/772 |
| 5,637,113 A | 6/1997 | Tartaglia et al. ............. 623/1 |
| 5,639,278 A | 6/1997 | Dereume et al. ............. 623/1 |
| 5,649,977 A | 7/1997 | Campbell .................. 623/1 |
| 5,674,241 A | 10/1997 | Bley et al. ................ 606/198 |
| 5,688,516 A | 11/1997 | Raad et al. ................ 424/409 |
| 5,690,670 A | 11/1997 | Davidson .................. 606/198 |
| 5,697,967 A | 12/1997 | Dinh et al. .................. 623/1 |
| 5,700,286 A | 12/1997 | Tartaglia et al. ............. 623/1 |
| 5,702,682 A | 12/1997 | Thompson ................ 424/9.42 |
| 5,421,955 A | 1/1998 | Lau et al. ................... 216/48 |
| 5,707,388 A | 1/1998 | Lauterjung ................ 606/198 |
| 5,713,949 A | 2/1998 | Jayaraman .................. 623/1 |
| 5,716,406 A | 2/1998 | Farber ....................... 623/11 |
| 5,718,723 A | 2/1998 | Matsuda et al. .............. 623/1 |
| 5,718,726 A | 2/1998 | Amon et al. .................. 623/2 |
| 5,725,672 A | 3/1998 | Schmitt et al. ............. 118/715 |
| 5,730,733 A | 3/1998 | Mortier et al. ............. 604/280 |
| 5,735,892 A | 4/1998 | Myers et al. ................. 623/1 |
| 5,741,327 A | 4/1998 | Frantzen ..................... 623/1 |
| 5,749,880 A | 5/1998 | Banas et al. .............. 606/198 |
| 5,750,206 A | 5/1998 | Hergenrother et al. ...... 427/490 |
| 5,759,192 A | 6/1998 | Saunders .................. 606/194 |
| 5,762,625 A | 6/1998 | Igaki ........................... 604/8 |
| 5,766,710 A | 6/1998 | Turnlund et al. .......... 428/36.1 |
| 5,769,884 A | 6/1998 | Solovay ...................... 623/1 |
| 5,776,161 A | 7/1998 | Globerman ................ 606/194 |
| 5,780,807 A | 7/1998 | Saunders |
| 5,788,626 A | 8/1998 | Thompson .................. 600/36 |
| 5,789,018 A | 8/1998 | Engelson et al. ............ 427/2.3 |
| 5,795,626 A | 8/1998 | Gabel et al. |
| 5,800,507 A | 9/1998 | Schwartz ...................... 623/1 |
| 5,810,868 A | 9/1998 | Lashinski et al. ........... 606/194 |
| 5,810,870 A | 9/1998 | Myers et al. ............... 606/198 |
| 5,824,046 A | 10/1998 | Smith et al. ................... 623/1 |
| 5,824,048 A | 10/1998 | Tuch ............................. 623/1 |
| 5,824,057 A | 10/1998 | Plaiá et al. .................... 623/1 |
| 5,833,651 A | 11/1998 | Donovan et al. ............. 604/53 |
| 5,836,966 A | 11/1998 | St. Germain ............... 606/198 |
| 5,837,316 A | 11/1998 | Fuchita ...................... 427/191 |
| 5,843,118 A | 12/1998 | Sepetka et al. ............ 606/194 |
| 5,843,120 A | 12/1998 | Israel et al. ............... 606/198 |
| 5,843,164 A | 12/1998 | Frantzen et al. ............... 623/1 |
| 5,843,171 A | 12/1998 | Campbell et al. .............. 623/1 |
| 5,868,783 A | 2/1999 | Tower ........................ 606/198 |
| 5,869,127 A | 2/1999 | Zhong ...................... 427/2.12 |
| 5,902,290 A | 5/1999 | Peacock, III et al. ........ 604/282 |
| 5,913,895 A | 6/1999 | Burpee et al. .................. 623/1 |
| 5,928,279 A | 7/1999 | Shannon et al. ............... 623/1 |
| 5,951,513 A | 9/1999 | Miraki ......................... 604/96 |
| 5,961,545 A | 10/1999 | Lentz et al. .................... 623/1 |
| 5,961,546 A | 10/1999 | Robinson et al. .............. 623/1 |
| 5,964,730 A | 10/1999 | Williams et al. ............. 604/103 |
| 5,968,070 A | 10/1999 | Bley et al. ................. 606/198 |
| 5,976,179 A | 11/1999 | Inoue ............................ 623/1 |
| 5,980,565 A | 11/1999 | Jayaraman .................... 623/1 |
| 5,980,566 A | 11/1999 | Alt et al. ....................... 623/1 |
| 5,993,489 A | 11/1999 | Lewis et al. ................... 628/1 |
| 6,004,310 A | 12/1999 | Bardsley et al. ............. 604/254 |
| 6,010,521 A | 1/2000 | Lee et al. ................... 606/194 |
| 6,010,529 A | 1/2000 | Herweck et al. ............... 623/1 |
| 6,010,530 A | 1/2000 | Goicoechea ................... 623/1 |
| 6,013,100 A | 1/2000 | Inoue ............................ 623/1 |
| 6,015,429 A | 1/2000 | Lau et al. ....................... 623/1 |
| 6,015,430 A | 1/2000 | Wall .............................. 623/1 |
| 6,019,789 A | 2/2000 | Dinh et al. ..................... 623/1 |
| 6,025,034 A | 2/2000 | Strutt et al. ................. 427/450 |
| 6,027,526 A | 2/2000 | Limon et al. ............... 606/198 |
| 6,042,597 A | 3/2000 | Kveen et al. ............... 604/526 |
| 6,059,770 A | 5/2000 | Peacock, III et al. ........... 623/1 |
| 6,074,135 A | 6/2000 | Tapphorn et al. |
| 6,090,134 A | 7/2000 | Tu et al. ................... 623/1.16 |
| 6,099,559 A | 8/2000 | Nolting .................... 623/1.43 |
| 6,099,561 A | 8/2000 | Alt ........................... 623/1.13 |
| 6,120,536 A | 9/2000 | Ding et al. ................ 623/1.13 |
| 6,139,573 A | 10/2000 | Sogard et al. ............. 623/1.44 |
| 6,143,022 A | 11/2000 | Shull et al. ............... 623/1.13 |
| 6,143,370 A | 11/2000 | Panagiotou et al. ......... 427/422 |
| 4,776,337 A | 12/2000 | Palmaz ....................... 606/108 |
| 6,156,064 A | 12/2000 | Chouinard ................ 623/1.12 |
| 6,159,239 A | 12/2000 | Greenhalgh ................ 623/1.12 |
| 6,162,244 A | 12/2000 | Braun et al. ............... 623/1.12 |
| 6,165,211 A | 12/2000 | Thompson ................ 623/1.13 |
| 6,168,619 B1 | 1/2001 | Dinh et al. ................ 623/1.13 |
| 6,174,330 B1 | 1/2001 | Stinson ..................... 623/1.34 |
| 6,184,266 B1 | 2/2001 | Ronan et al. ............... 523/113 |
| 6,241,691 B1 | 6/2001 | Ferrera et al. .............. 600/585 |
| 6,251,136 B1 | 6/2001 | Guruwaiya et al. ........ 623/1.46 |
| 6,368,658 B1 * | 4/2002 | Schwarz et al. ........... 427/2.15 |
| 6,431,464 B2 * | 8/2002 | Seitz ............................ 239/80 |
| 6,432,133 B1 | 8/2002 | Lau et al. |
| 6,447,848 B1 | 9/2002 | Chow et al. ................. 427/446 |
| 6,502,767 B2 * | 1/2003 | Kay et al. ................... 239/433 |
| 6,774,278 B1 | 8/2004 | Ragheb et al. |
| 2002/0032477 A1 * | 3/2002 | Melmus et al. ............. 623/1.2 |
| 2002/0042645 A1 | 4/2002 | Shannon ................... 623/1.13 |
| 2002/0138136 A1 | 9/2002 | Chandresekaran et al. . 623/1.34 |
| 2004/0088038 A1 * | 5/2004 | Dehnad et al. ............ 623/1.15 |

FOREIGN PATENT DOCUMENTS

| | | |
|---|---|---|
| CA | 2007648 | 4/1991 |
| CA | 1322628 | 10/1993 |
| CA | 1336319 | 7/1995 |
| CA | 1338303 | 5/1996 |
| EP | 0 045 627 A1 | 2/1982 |
| EP | 0 201 466 A2 | 11/1986 |
| EP | 0 221 570 A2 | 5/1987 |
| EP | 0 335 341 B1 | 10/1989 |
| EP | 0 338 816 A2 | 10/1989 |
| EP | 0 351 314 B1 | 1/1990 |
| EP | 0 357 003 A2 | 3/1990 |
| EP | 0 364 787 A1 | 4/1990 |
| EP | 0 372 789 A3 | 6/1990 |
| EP | 0 380 668 B1 | 8/1990 |
| EP | 0 407 951 A2 | 1/1991 |
| EP | 0 421 729 A2 | 4/1991 |
| EP | 0 423 916 A1 | 4/1991 |
| EP | 0 517 075 B1 | 12/1992 |
| EP | 0 540 290 A2 | 5/1993 |
| EP | 0 540 290 B1 | 5/1993 |
| EP | 0 565 251 | 10/1993 |
| EP | 0 604 022 A1 | 6/1994 |
| EP | 0 606 165 A1 | 7/1994 |
| EP | 0 621 017 A1 | 10/1994 |
| EP | 0 649 637 A1 | 4/1995 |
| EP | 0 701 802 A1 | 3/1996 |
| EP | 0 716 836 A1 | 6/1996 |
| EP | 0 756 853 A1 | 2/1997 |
| EP | 0 800 801 A1 | 10/1997 |
| EP | 0 806 190 A1 | 11/1997 |
| EP | 0 824 900 A2 | 2/1998 |
| EP | 0 832 618 A1 | 4/1998 |
| EP | 0 916 317 A1 | 5/1999 |
| EP | 0 938 879 A2 | 9/1999 |
| GB | 2 070 490 A | 9/1981 |
| GB | 2 135 585 A | 4/1982 |
| JP | 49-48336 | 12/1974 |
| JP | 54-18317 | 7/1979 |
| JP | 58-501458 | 9/1983 |
| JP | 60-28504 | 7/1985 |
| JP | 62235496 A | 10/1987 |
| JP | 63-214264 | 9/1988 |
| JP | 62-242292 | 3/1989 |
| JP | 02-174859 | 7/1990 |
| JP | 02-255157 | 10/1990 |

| | | |
|---|---|---|
| JP | 03009746 A | 1/1991 |
| JP | 04-25755 | 2/1992 |
| JP | 18-33718 | 2/1996 |
| JP | 10151190 A | 6/1998 |
| WO | WO 91/07139 | 5/1991 |
| WO | WO 91/17789 | 11/1991 |
| WO | WO 92/06734 | 4/1992 |
| WO | WO 92/09246 | 6/1992 |
| WO | WO 93/06792 | 4/1993 |
| WO | WO 94/17754 | 8/1994 |
| WO | WO 95/11817 | 5/1995 |
| WO | WO 95/23563 | 9/1995 |
| WO | WO 95/26695 | 10/1995 |
| WO | WO 96/00103 | 1/1996 |
| WO | WO 96/09013 | 3/1996 |
| WO | WO 96/28115 | 9/1996 |
| WO | WO 97/10011 | 3/1997 |
| WO | WO 97/25937 | 7/1997 |
| WO | WO 98/20927 | 5/1998 |
| WO | WO 98/22159 | 5/1998 |
| WO | WO 98/32412 | 7/1998 |
| WO | WO 98/58600 | 12/1998 |
| WO | WO 99/17680 | 4/1999 |
| WO | WO 99/39661 | 8/1999 |

OTHER PUBLICATIONS

McCune, R.C., et al.; "An Exploration of the Gold Gas-Dynamic Spray Method for Several Materials Systems," *Proceedings of the 8th National Thermal Spray Conference*—Houston, Texas, Sep. 11-15, 1995, pp. 1-5.

Wilcox, B.A.; "Report on: Conference on Thermal Spray Processing of Nanoscale Materials, Davos, Switzerland, Aug. 4-7, 1997," *European Materials Science and Engineering—Office of Naval Research—European Office*, Sep. 18, 1997.

Sampath, S., et al.; "Thermal-Spray Processing of Materials," *MRS Bulletin*, Jul. 2000, pp. 12-16.

Herman, H., et al.; "Thermal Spray: Current Status and Future Trends," *MRS Bulletin*, Jul. 2000, pp. 17-25.

Fincke, J. R., et al.; "Advanced Diagnostics and Modeling of Spray Processes," *MRS Bulletin*, Jul. 2000, pp. 26-31.

Vardelle, A., et al.; "The Dynamics of Deposit Formation in Thermal-Spray Processes," *MRS Bulletin*, Jul. 2000, pp. 32-37.

Gitzhofer, F., et al.; "Integrated Fabrication Processes for Solid-Oxide Fuel Cells using Thermal Plasma Spray Technology," *MRS Bulletin*, Jul. 2000, pp. 38-42.

Zhu, D., et al.; "Thermal-Barrier Coatings for Advanced Gas-Turbine Engines," *MRS Bulletin*, Jul. 2000, pp. 43-47.

Brogan, J. A.; "Thermal-Spraying of Polymers and Polymer Blends," *MRS Bulletin*, Jul. 2000, pp. 48-53.

Web site: http://doL1.eng.sunysb.edu/Berndt/Berndt-NP14/html; "Thermal Spray as a Means to Achieve Nano-Phased Structures," Nov. 27, 2000, 30 pages.

Web site: http//homepage.dtn.ntl.com/gordon.england/tsc.html; "Nature of Thermal Spray Coatings," Nov. 29, 2000, 9 pages.

"Thermal Spray Technology," ITSC 2000, *Advanced Materials & Processes*, Aug. 2000, pp. 45-48.

Berndt, C.C.; "Thermal Spray Processing of Nanoscale Materials II—Extended Abstract," *Journal of Thermal Spray Technology*, vol. 10(1), Mar. 2001, pp. 147-180.

Saravanan, P., et al.; "Experimental Study of Particle Deposition Characteristics of Alumina Using Plasma Spraying," *Journal of Thermal Spray Technology*, vol. 10(1), Mar. 2001, pp. 138-141.

"Cold Spray is Highlighted at Fifth HVOF Conference—Nov. 2000, Erding, Germany," *Journal of Thermal Spray Technology*, vol. 10(2), Jun. 2001, pp. 216-217.

Llorca-Isern, N., et al.; "Estimation of Three-Dimensional Connectivity of Internal Defects in Coatings Using Fractal Analysis," *Journal of Thermal Spray Technology*, vol. 10(2), Jun. 2001, pp. 287-292.

Kuroda, S., et al.; "Peening Action and Residual Stresses in High-Velocity Oxygen Fuel Thermal Spraying of 316L Stainless Steel," *Journal of Thermal Spray Technology*, vol. 10(2), Jun. 2001, pp. 367-374.

Wan, Y. P, et al.; "Modeling and Visualization of Plasma Spraying of Functionally Graded Materials and Its Application tot he Optimization of Spray Conditions," *Journal of Thermal Spray Technology*, vol. 10(2), Jun. 2001, pp. 382-389.

"Selected Abstracts of Thermal Spray Literature," *Journal of Thermal Spray Technology*, vol. 10(2), Jun. 2001, pp. 390-391 and 398-399.

"GTS Advances on Cold Spray Technology," *Journal of Thermal Spray Technology*, vol. 10(3), Sep. 2001, pp. 434-435.

"Selected Abstracts of Thermal Spray Literature," *Journal of Thermal Spray Technology*, vol. 10(3), Sep. 2001, pp. 532-538.

*Journal of Thermal Spray Technology*, vol. 10(4), Dec. 2001, pp. 555-558, 562, 565, 566, 568-571.

"Selected Abstracts of Thermal Spray Literature," *Journal of Thermal Spray Technology*, vol. 10(4), Dec. 2001, pp. 673-691.

*Journal of Thermal Spray Technology*, vol. 11(1), Mar. 2002, pp. 13-14, 27-28.

Hollahan, et al., Attachment of Amino Groups to Polymer Surfaces by Radiofrequency Plasmas, *Journal of Applied Polymer Science*, vol. 13, pp. 807-816 (1969).

Rösch, J., M.D., et al., Transjugular Intrahepatic Portacaval Shunt: an Experimental Work, *The American Journal of Surgery*, pp. 588-592, vol. 121, May 1971.

Dotter, Charles T., Transluminal Expandable Nitinol Coil Stent Grafting: Preliminary Report, *Radiology Journal*, pp. 259-260, Apr. 1983.

70th Scientific Assembly and Annual Meeting: Scientific Program, *Radiology*, Washington, DC: Nov. 25-30, 1984, Special Edition, 153(P).

C. R. Bard, Pe Plus Peripheral Balloon Dilatation Catheter, *C. R. Bard, Inc.*, Aug. 1985.

Wright, et al., Percutaneous Endovascular Stents: an Experimental Evaluation, *Radiology Journal*, pp. 69-72, 1985.

Palmaz, et al., Expandable Intraluminal Graft; a Preliminary Study, *Radiology Journal*, pp. 73-77, 1985.

Program: Day 2 (Nov. 18) the Radiological Society of North America, *Radiology*, 1985.

Charnsangavej, C., M.D., et Al., Endovascular Stent for Use in Aortic Dissection: an in Vitro Experiment, *Radiology*, pp. 323-324, vol. 157, No. 2, Nov. 1985.

Wallace, Michael J., et al., Tracheobronchial Tree: Expandable Metallic Stents Used in Experimental and Clinical Applications (Work in Progress), *Radiology*, pp. 309-312, vol. 158, Feb. 1986.

72nd Scientific Assembly and Annual Meeting: RSNA Scientific Program, *Radiology*, Chicago: Nov. 30-Dec. 5, 1986, Special Edition vol. 161(P).

Duprat, et al., Flexible Balloon-Expanded Stent for Small Vessels, *Radiology Journal*, pp. 276-278, 1987.

Rösch, Josef, M.D., et al., *Gianturco Expandable Stents in Experimental and Clinical Use*, paper presented at The Twelfth Annual Course on "Diagnostic Angiography and Interventional Radiology" Mar. 23-26, 1987 (San Diego, California).

Rösch, Joseph, M.D., et al., Gianturco Expandable Wire Stents in the Treatment of Superior Vena Cava Syndrome Recurring after Maximum-tolerance Radiation, *Cancer*, pp. 1243-1246, vol. 60, Sep. 1987.

Yoshioka, Tetsuya, et al., Self-expanding Endovascular Graft: an Experimental Study in Dogs, *American Journal of Roentgeriology*, pp. 673-676, vol. 151, Oct. 1988.

Yoshioka, et al., Development And Clinical Application of Biliary Endoprostheses Using Expandable Metallic Stents, *Japan Radiological Society*, 1988, vol. 48, No. 9, pp. 1183-1185 (with translation).

Mirich, et al., Percutaneously Placed Endovascular Grafts for Aortic Aneurysms: Feasibility Study, *Radiology*, 1989, Part 2, pp. 1033-1037.

Inagaki, et al., Hydrophilic Surface Modification of Polyethylene by No-Plasma Treatment, *Adhesion Science Technology*, Nov. 1989, vol. 4, No. 2, pp. 99-107.

Gölander, et al., RF-Plasma-Modified Polystyrene Surfaces for Studying Complement Activation, *J. Biomater. Sci. Polymer Edn.*, vol. 4, No. 1, pp. 25-30 (1992).

Poncin-Epaillard, et al., Reactivity of a Polypropylene Surface Modified in a Nirtogen Plasma, *Plasma Surface Modification of Polymers*, pp. 167-180 (1994).

Gengenbach, et al., Evolution of the Surface Composition and Topography of Perfluorinated Polymers Following Ammonia-Plasma Treatment, *Plasma Surface Modification of Polymers*, pp. 123-146 (1994).

Lambert, et al., Localized Arterial Wall Drug Delivery From a Polymer-Coated Removable Metallic Stent, *Circulation*, vol. 90, No. 2 pp. 1003-1011 (Aug. 1994).

De Scheerder, et al., Biocompatibility of Polymer-Coated Oversized Metallic Stents Implanted in Normal Porcine Coronary Arteries, *Atherosclerosis*, vol. 114, pp. 105-114 (1995).

Union Carbide Technology Letter, New Busiiness Department—Parylene, Oct. 1973, No. 7 (8 pages).

Union Carbide, Electronic Materials, Parylene Products, Oct. 1973, No. 9 (23 pages).

Union Carbide Technology Letter, May 1974, No. 11 (12 pages).

Union Carbide Technology Letter, Oct. 1975, No. 15 (13 pages).

Union Carbide, Electronic Materials, Parylene Products, Mar. 1976, No. 16 (4 pages).

Eskin, et al., Growth of Cultured Calf Aortic Smooth Muscle Cells on Cardiovascular Prosthetic Materials, *Journal of Biomedical Material Research*, vol. 10, pp. 113-122 (1976).

Loeb, et al., *Parylene as a Chronically Stable, Reproducible Microelectrode Insulator*, IEEE Transactions on Biomedical Engineering, pp. 121-128 ( Mar. 1977).

Union Carbide, Electronic Materials, Parylene Products, Aug. 1977, No. 18 (7 pages).

Union Carbide, Electronic Materials, Parylene Products, Oct. 1977, No. 1, Revision 2 (7 pages).

Union Carbide, Electronic Materials, Parylene Products, Oct. 1977, No. 2, Revision 1 (9 pages).

Union Carbide, Electronic Materials, Parylene Products, Oct. 1977, No. 3 (21 pages).

Union Carbide, Electronic Materials, Parylene Products, Oct. 1977, No. 4, (13 pages).

Union Carbide, Electronic Materials, Parylene Products, Oct. 1977, No. 6 (12 pages).

Union Carbide, Electronic Materials, Parylene Products, Oct. 1977, No. 7, Revision 1 (8 pages).

Union Carbide, Electronic Materials, Parylene Products, Oct. 1977, No. 8, Edited (19 pages).

Union Carbide, Electronic Materials, Parylene Products, Oct. 1977, No. 10 (50 pages).

Union Carbide, Electronic Materials, Parylene Products, Oct. 1977, No. 11 (12 pages).

Union Carbide, Electronic Materials, Parylene Products, Oct. 1977, No. 12, Revision 1 (6 pages).

Union Carbide, Electronic Materials, Parylene Products, Oct. 1977, No. 13, Revision 1 (7 pages).

Union Carbide, Electronic Materials, Parylene Products, Oct. 1977, No. 14, Revision 1 (11 pages).

Union Carbide, Electronic Materials, Parylene Products, Oct. 1977, No. 15, Revision 1 (8 pages).

Union Carbide, Electronic Materials, Parylene Products, Oct. 1977, No. 17, Revision 1 (11 pages).

ISEEE Transactions on Biomedical Engineering, vol. BME-27, No. 11, Nov. 1980 (5 pages).

Sadhir, et al., The Adhesion of Glow-Discharge Polymers, Silastic and Parylene to Implantable Platinum Electrodes: Results of Tensile Pull Tests After Exposure to Isotonic Sodium Chloride, vol. 2, *Biomaterials*, pp. 239-243 (Oct. 1981).

Hahn, et al., *Glow Discharge Polymers as Coatings for Implanted Devices*, John M. Dlaton Research Center, University of Missouri-Columbia and the Graduate Center for Materials Research, pp. 109-113 (1981).

Union Carbide, Electrode Materials, Parylene Products, Jan. 18, 1982, No. 5, Revision 4 (17 pages).

Hahn, et al., Biocompatibility of Glow-Discharge-Polymerized Films and Vacuum-Deposited Parylene, *Journal of Applied Polymer Science: Applied Polymer Symposium* 38, 55-64 (1984).

Casper, et al., Fiber-Reinforced Absorbable Compsite for Orthopedic Surgery, *Polymeric Materials Science and Engineering*, Proceedings of the ACS Division of Polymeric Materials: Science and Engineering, vol. 53, Fall Meeting 1985.

Kelley, B.S. et al., Totally Resorbable High-Strength Composite Mateiral, *Advances in Biomedical Polymers*, Edited by Charles G. Gebelein (1987).

Yuen, et al., *Tissue Response to Potential Neuroprosthetic Materials Implanted Subdurally, Biomaterials*, vol. 8, pp. 57-62 (Mar. 1987).

Nichols, et al., *Electrical Insulation of Implantable Devices by Composite Polymer Coatings*, Dalton Research Center, University of Missouri, 1987.

Schmidt, et al., *Long-Term Implants of Parylene-C Coated Microelectrodes, Medical & Biological Engineering and Computing*, pp. 96-101 (Jan. 1988).

Olson, Parylene, *A Biostable Coating for Medical Applications*, for NOVA TRAN Parylene Coating Services (Jul. 25, 1988; Nov. 14, 1988).

Beach, et al., *Xylylene Polymers*, Encyclopedia of Polymer Science and Engineering, vol. 17, Second Edition, pp. 990-1025, 1989.

Muller, et al., Advanced in Coronary Angioplasty: Endovascular Stents, *Coronary Artery Disease*, vol. 1, No. 4, Jul./Aug. 1990.

Loh, et al., Plasma Enhanced Parylene Deposition, *Antec*, pp. 1099-1103 (1991).

Gebelein, et al., (ed), Biomedical and Dental Applications of Polymers, *Polymer Science and Technology*, vol. 14, pp. 143-161 (No date).

Wong, et al., An Update on Coronary Stents, *Cardio*, Feb. 1992.

The Parylene Press (A Publication of Specialty Coating Systems, Inc.), Winter 1992 (7 pages).

Charlson, et al., Temperature Selective Deposition of Parylene-C, *IEEE Transactions on Biomedical Engineering*, vol. 39, No. 2, pp. 202-206, (Feb. 1992).

Bull, Parylene Coating for Medical Applications *Medical Product Manufacturing News*, Mar. 1993 (2 pages).

The Parylene Press (A Publication of Specialty Coating Systems, Inc.), Spring 1993 (6 pages).

The Parylene Press (A Publication of Specialty Coating Systems, Inc.), Summer 1993 (4 pages).

*Information Regarding Parylene-C Coating for ACS Metal Stent*, In-Home Memorandum from Ed Newton to Joe Callol, Mike Clayman, Dennis Houlsby and Joe Tartaglia, Oct. 15, 1993 attaching Parylene, a Biostable Coating for Medical Application by Roger Olson.

Moody: Vacuum Coating Ultrasonic Transducers, *Sensors*, Dec. 1993 (1 page).

Union Carbide A-174 Silane, Sales Brochure, Union Carbide Adhesion Promoters, Jan. 1968 (5 pages).

Parylene Conformal Coatings Specifications and Properties, Sales Brochure, Union Carbide Specialty Coating Systems (12 pages).

Parylene Environmentally Compatible Conformal Coatings for Electronic Components Assemblies and Precision Parts, Brochure, Union Carbide Electronics Division (14 pages).

Parylene and Nova Tran™ Parylene Coating Services, for Unmatched Conformal Coating Performance, Brochure, Union Carbide Specialty Coating Systems (21 pages).

Nova Tran™ Custom Coating Services, Parylene Conformal Coating, Brochure, Union Carbide (8 pages).

Parylene, a Biostable Coating for Medical Applications, Brochure, Union Carbide Specialty Coating Systems (6 pages).

Typical Parylene Properties, Printout, Para Tech Coating Company; Lab Top® Parylene Deposition System Model 3000, Sales Brochure, Para Tech Coating Company (7 pages).

Dotter, Charles T., Transluminally-Placed Coilspring Endarterial Tube Grafts: Long-Term Patency in Canine Popliteal Artery, *Investigative Radiology*, Sep./Oct. 1969, pp. 329-332.

Cragg, Andrew, M.D., et al., Nonsurgical Placement of Arterial Endoprostheses: A New Technique Using Nitinol Wire, *Radiology Journal*, Apr. 1983, pp. 261-263.

Maas, D., et al., Radiological Follow-Up of Transluminally Inserted Vascular Endoprostheses: An Experimental Study Using Expanding Spirals, *Radiology Journal*, Sep. 1984, pp. 659-663, vol. 152, No. 3.

Khor et al., *The Thermal Spray Processing of HA Powders and Coatings*, Journal of Materials, The Metallurgical Society, Feb. 1997, pp. 51-57.

Sandia National Laboratories, News Release, *Industry warm up to promises of Cold Spray ™, Sandia explores frontiers of 'splat science,'* www.sandia.gov/media/NewsRel/NR2001, Jun 25, 2001, pp. 1-3.

Yang et al., *Deposition of highly adhesive ZrO2 coating on Ti and CoCrMo implant materials using plasma spraying*, Biomaterial 24 (2003), pp.619-627.

\* cited by examiner

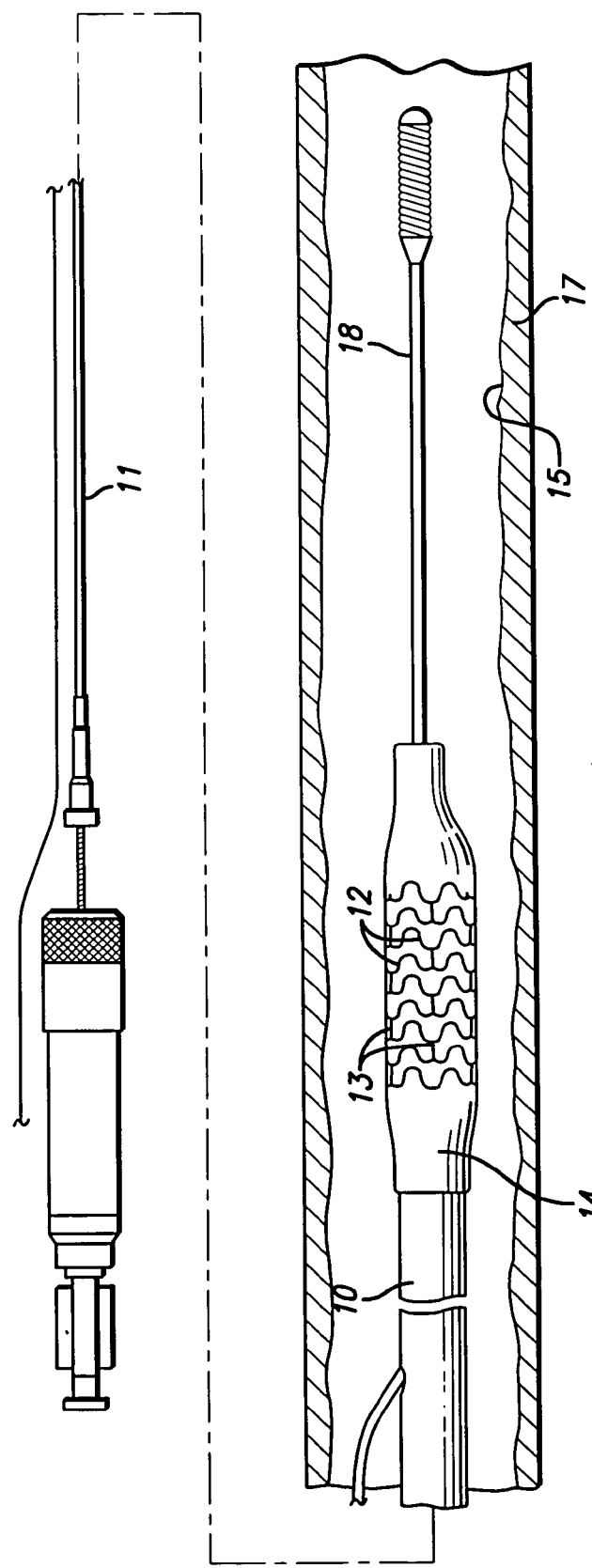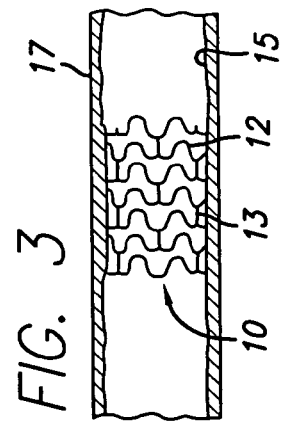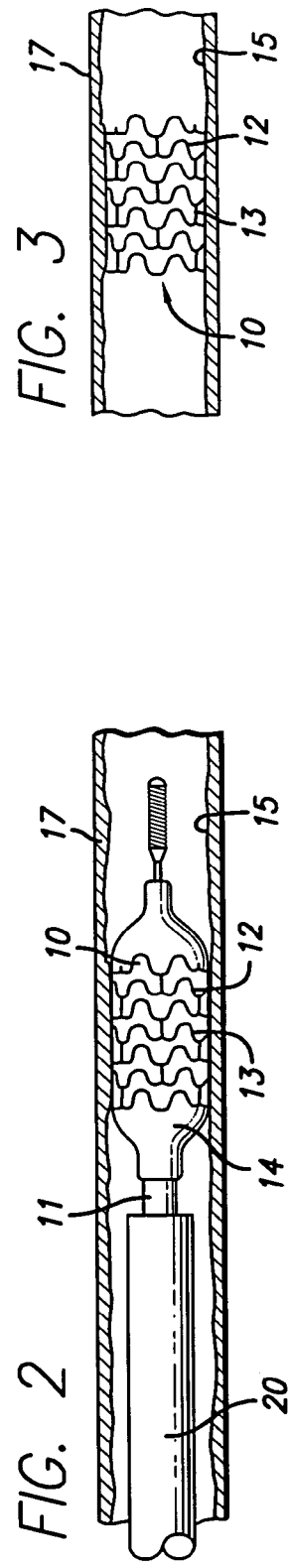

METHOD AND APPARATUS FOR THERMAL SPRAY PROCESSING OF MEDICAL DEVICES

BACKGROUND OF THE INVENTION

This invention relates to medical devices and more particularly, the invention relates to methods of manufacturing and coating medical devices utilizing thermal spray processing (TSP).

Several interventional treatment modalities are presently used for heart disease, including balloon and laser angioplasty, atherectomy, and by-pass surgery. In typical coronary balloon angioplasty procedures, a guiding catheter having a distal tip is percutaneously introduced through the femoral artery into the cardiovascular system of a patient using a conventional Seldinger technique and advanced within the cardiovascular system until the distal tip of the guiding catheter is seated at the ostium of the coronary arteries. A guide wire is positioned within an inner lumen of a dilatation catheter and then both are advanced through the guiding catheter to the distal end thereof.

The guide wire is first advanced out of the distal end of the guiding catheter into the patient's coronary vasculature until the distal end of the guide wire crosses a lesion to be dilated, then the dilatation catheter having an inflatable balloon on the distal portion thereof is advanced into the patient's coronary anatomy over the previously introduced guide wire until the balloon of the dilatation catheter is properly positioned across the lesion.

Once in position across the lesion, the balloon is inflated to compress the plaque of the lesion against the inside of the artery wall and to otherwise expand the inner lumen of the artery. The balloon is then deflated so that blood flow can be resumed through the dilated artery and the dilatation catheter can be removed therefrom. Further details of dilatation catheters, guide wires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); U.S. Pat. No. 4,748,982 (Horzewski, et al.); U.S. Pat. No. 5,507,768 (Lau, et al.); U.S. Pat. No. 5,451,233 (Yock); and U.S. Pat. No. 5,458,651 (Klemm, et al.), which are hereby incorporated herein in their entirety by reference thereto.

One problem that can occur during balloon angioplasty procedures is the formation of intimal flaps which can collapse and occlude the artery when the balloon is deflated at the end of the angioplasty procedure. Another problem characteristic of balloon angioplasty procedures is the large number of patients who are subject to restenosis in the treated artery. In the case of restenosis, the treated artery may again be subjected to balloon angioplasty or to other treatments such as by-pass surgery, if additional balloon angioplasty procedures are not warranted. However, in the event of a partial or total occlusion of a coronary artery by the collapse of a dissected arterial lining after the balloon is deflated, the patient may require immediate medical attention, particularly in the coronary arteries.

A focus of recent development work in the treatment of heart disease has been directed to endoprosthetic devices referred to as stents. Stents are generally cylindrically shaped intravascular devices which are placed within an artery to hold it open. The device can be used to reduce the likelihood of restenosis and to maintain the patency of a blood vessel immediately after intravascular treatments. In some circumstances, they can also be used as the primary treatment device where they are expanded to dilate a stenosis and then left in place. Further details of stents can be found in U.S. Pat. No. 3,868,956 (Alfidi et al.); U.S. Pat. No. 4,512,338 (Balko et al.); U.S. Pat. No. 4,553,545 (Maass et al.); U.S. Pat. No. 4,733,665 (Palmaz); U.S. Pat. No. 4,762,128 (Rosenbluth); U.S. Pat. No. 4,800,882 (Gianturco); U.S. Pat. No. 4,856,516 (Hillstead); U.S. Pat. No. 4,886,062 (Wiktor); U.S. Pat. No. 5,421,955 (Lau); and U.S. Pat. No. 5,569,295 (Lam), which are hereby incorporated herein in their entirety by reference thereto.

One method and system developed for delivering stents to desired locations within the patient's body lumen involves crimping a stent about an expandable member, such as a balloon on the distal end of a catheter, advancing the catheter through the patient's vascular system until the stent is in the desired location within a blood vessel, and then inflating the expandable member on the catheter to expand the stent within the blood vessel. The expandable member is then deflated and the catheter withdrawn, leaving the expanded stent within the blood vessel, holding open the passageway thereof.

Commercially available 316L stainless steel tubing contains average grain sizes ranging from approximately 0.0025 inch (64 microns), ASTM grain size 5 to around 0.00088 inch (22 microns), ASTM grain size 8. These grain sizes result in anywhere from two to five grains across the tube thickness, and the stent subsequently manufactured from the tubing depending on the tube and stent strut thicknesses. Part of the limitation in achieving a finer grain size in this material arises from the number of draws and anneals the tubing must go through to achieve its final size. The potential for reducing the grain size exists by reducing the required number of heat-processing steps by reducing the starting size of the raw product that is then processed down into the tubing.

Lowering the grain size and increasing the number of grains across the strut thickness of a stent allows the grains within the stent to act more as a continuum and less as a step function. The ideal result of processing the material to a smaller grain size would result in an average grain size of between approximately 1 and 10 microns, with a subsequent average number of grains across the strut thickness about eight or greater. Likewise, other medical devices will benefit from a reduction in grain size such as guide wires, ring markers, defibrillator lead tips, delivery system devices such as catheters, and the like.

SUMMARY OF THE INVENTION

The present invention relates to methods of manufacturing and coating medical devices utilizing thermal spray processing (TSP). The process includes producing a coating having an average grain size of between 1 and 64 microns and providing a thin walled structure having a wall thickness of about eight or more grains. While the grain size for thin walled structures (such as stents) has been referred to herein as about eight or more grains, the number of grains does vary depending on wall thickness. Thus, for very thin walled structures the wall thickness may be between four and eight grains, but for most (but not all) stent applications it is desirable to have at least eight or more grains comprising the wall thickness.

The invention involves the use of TSP for the manufacture of fine grained tubing for subsequent use as a medical device such as a stent or other tubular or ring-based implant, the manufacture of intermediate size tube that may then be drawn into final size tubing, and for the coating of a stent or other medical device. Medical devices which will benefit from the present invention include stents, guide wires, ring markers, tubular or wire based implants, defibrillator lead tips, and catheters and other delivery system devices. While the present invention TSP is utilized for the medical devices described herein, stents will be used as an example of the inventive manufacturing process and coating process disclosed and claimed herein.

Thermal spray is a generic term for a broad class of related processes in which molten droplets of metals, ceramics, glasses, and/or polymers are sprayed onto a surface to produce a coating, to form a free-standing near-net-shape, or to create an engineered material with unique properties (e.g., strain-tolerant ceramics, metallic glasses, cermets, or metal/polymer composites).

In principle, any material with a stable molten phase can be thermally sprayed, and a wide range of pure and composite materials are routinely sprayed for both research and industrial applications. Deposition rates are very high in comparison to alternative coating technologies. Deposit thicknesses of 0.1 to 1 mm are common, and thicknesses greater than 1 cm can be achieved with some materials.

With regard to manufacturing, the invention relates to the overall manufacturing of tube stock and coatings, creating layered material and other materials through powder consolidation during spraying, with the additional potential of creating composite materials.

As mentioned above, commercially available 316L stainless steel tubing contains average grain sizes ranging from approximately 0.0025 inch (64 microns), ASTM grain size 5 to around 0.00088 inch (22 microns), ASTM grain size 8. These grain sizes result in anywhere from two to five grains across the tube thickness, and the stent subsequently manufactured from this tubing depending on the tube and stent strut thicknesses. Part of the limitation in achieving a finer grain size in this material arises from the number of draws and anneals the tubing must go through to achieve its final size. The potential for reducing the grain size exists by reducing the required number of heat-processing steps by reducing the starting size of the raw product that is then processed down into the tubing.

Lowering the grain size and increasing the number of grains across the strut thickness allows the grains within the stent to act more as a continuum and less as a step function. For example, the result of processing the material to a smaller grain size in a stent would result in an average grain size of between approximately 1 and 64 microns, with a subsequent average number of grains across the strut thickness about eight or greater. The average number of grains in a cross-section of a medical device depends upon the size of the device and the diameter of the grains.

In one embodiment, the manufacturing process includes thermal spray processing. Thermal spray processing can be generally defined as a group of processes in which finely divided metallic or nonmetallic surfacing materials are deposited in a molten or semi-molten condition on a substrate to form a spray deposit. Cold spray thermal processing, to be discussed herein, is considered a thermal spray process although the materials projected onto a surface are not necessarily molten or semi-molten. TSP includes several variants such as cold spraying, combustion spraying, arc spraying, high velocity oxy-fuel spraying, and plasma spraying. Currently sprayed materials include elements, metallic alloys, ceramics, composites and polymers. TSP can be considered to be a net or near net shaped process. This means that the product that comes out of the thermal spray process is close to or at the desired size and shape of the final product. This process can be used not only to coat a stent but also to manufacture tube stock that is used in place of gun drilled or extruded rod or subsequent tube manufacturing. Some factors to consider when spray forming include the grain size, porosity, and dimensional tolerances of the sprayed part. Post-processing can assist when one or more of these factors is not as desired for the final product. Thus TSP processing is presented here both with and without post-processing of the material.

Some advantages of thermal processing include the versatility with respect to feed materials (metals, ceramics, and polymers in the form of wires, rods, or powders); the capacity to form barrier and functional coatings on a wide range of substrates; the ability to create freestanding structures for net-shape manufacturing of high-performance ceramics, composites, and functionally graded materials; and the rapid-solidification synthesis of specialized materials.

TSP may be used to spray-form tube stock on top of a removable mandrel. The thickness of the tube may be varied by spraying more or less material, and the inner diameter dimensions may be varied by changing the size of the mandrel. The inner mandrel may be made of a substance that melts out or that is coated with a substance that allows easy removal of the finished sprayed tube. If the grain size, porosity, and dimensional tolerances (including wall runout, wall thickness, concentricity and surface roughness) are as desired, the mandrel may be removed and the sprayed tube is ready for further processing into a stent or other tubular or ring-shaped product. To create a ring-shaped product from a tube product, the tube is sprayed to the desired dimensions and then sliced in the transverse direction to result in rings of the desired size.

There are several potential post-processing operations that may take place on a sprayed tube. Grain size, porosity, and final dimensions are a few of the incentives for performing post processing.

Grain size of the finished tube depends on numerous factors, including the size of the particles being sprayed, the formation, impact and rate of solidification of the sprayed material, and the length of time the material is heated above a temperature that allows significant grain growth. For a metallic tube, if the grain size is larger than desired, the tube may be swaged to introduce heavy dislocation densities, then heat treated to recrystallize the material into finer grains. Alternatively, different material forms may be taken through a drawing or other working and heat treat processes to recrystallize the tubing. The type and amount of working allowed depends on the material, e.g., ceramics may require a high temperature working step while metals and composites may be workable at room temperature. Grain-size strengthening is where there is an increase in strength of a material due to a decrease in the grain size. The larger grain-boundary area more effectively blocks dislocation movement. The outer diameter of the tube usually requires a machining step of some sort to smooth the surface after the swaging process, and the same may be true before the tubing can be properly drawn.

By the very nature of the spray processing itself, the sprayed material may contain porosity, or small voids. These may be minimized or eliminated through control of the TSP parameters. The potential exists that the tube may need to be post-processed to eliminate this feature. One potential method of post processing involves a traveling ring furnace, where the material is melted and re-solidified as the ring travels down the length of the tube. This method requires close control to prevent preferential segregation of elements along with the melt pool. Another method is to process the material under high mechanical pressure to sinter the grains together; this method is generally used for powder processing. As porosity is difficult to remove from a material, however, the best form of elimination is to ensure that the TSP parameters are such that the porosity is not present in the first place.

While TSP is a near-net shape process, variability in the process itself may require post-processing so that the product achieves the required dimensional tolerances. Such processing may include machining of some form or centerless grinding the outer diameter of the sprayed tube to reduce wall thickness variability and to improve the surface finish. The inner diameter dimensions and surface finish should be dependant on the mandrel that it is sprayed on. If the starting size of the sprayed tube is large enough, it may be desirous to bore and ream or just ream the inner diameter for both dimension and surface roughness improvement. An alternate method is to perform a drawing operation on the TSP tube to draw the tube to the desired final size. In this case, if the outer diameter is too rough, the tube will need to be machined or ground prior to the drawing operation.

With regard to coatings, TSP may be used to coat an object with a desired material. The thickness of the coating may be varied by spraying more or less material, and this thickness may be varied along the length and around the diameter of the product. The advantage of using TSP as a coating process is the wide variety of materials that may be sprayed, including metallic elements, known and novel metallic alloys, ceramics, composites and polymers. The potential exists to spray stents, guide wires, and other products that require a coating. If the grain or node size, material density or porosity, and dimensional tolerances are as desired, the part should be ready for any post-passivation or other desired steps if the coating is considered to be an intermediate step in finishing the part.

Several potential post-processing operations may be used on a coated part. Grain or node size, material density or porosity, and final dimensions will be considered here as the parameters for performing post-processing.

Grain size or node size of the finished coating will depend on numerous factors, including the size of the particles being sprayed, the formation, impact and rate of solidification of the sprayed material, and the length of time the material is heated above a temperature that allows significant grain growth.

For a metallic coating, one modification to grain size that may be made is to heat treat the coating and grow the grains. It is generally difficult to work the stent and coating material in a way that introduces a high dislocation density that may then be used to recrystallize the material. For a metallic wire coating, the wire may be swaged or drawn to produce a higher dislocation density, then annealed to recrystallize to a smaller grain size; the same may be true of a tube that is coated. For a ceramic coating, heating may be a post-processing step, while for a polymeric coating, further cross-linking may be necessary.

As mentioned above the sprayed material may contain porosity, or small voids. These may be minimized or eliminated through control of the TSP parameters. The potential exists that the part may need to be post-processed to eliminate this feature. One potential method of post processing a metallic, ceramic or composite coating involves a traveling ring furnace where the material is melted and re-solidified as the ring travels down the length of the part. This method requires close control to prevent preferential segregation of elements along with the melt pool as well as to prevent unwanted migration of the coating into the underlying material. Another method would be to process the material under high mechanical pressure in a vacuum to sinter the grains together. This method is generally used for powder processing. As porosity is difficult to remove from a material if "no porosity" is a coating requirement, the best form of elimination would be to ensure that the TSP parameters are such that the porosity is not present in the first place.

While TSP is a near-net shape process, variability in the process itself may require post-processing to finalize the coating to required dimensional tolerances. Mechanical post-processing of a stent would be difficult because of the diminutive nature of the stent. Post-processing of or tubular product is less difficult. For the latter products, outer diameter processing may include machining, e.g., centerless grinding, or drawing to reduce coating thickness variability and to improve the surface finish. If a part is sprayed on the inner diameter, it may be desirous to machine out the inner diameter by, for example, boring and/or reaming, for both dimension and surface roughness improvement.

As mentioned above, thermal spray processing (TSP) includes several variants such as cold spraying, combustion spraying, arc spraying, high velocity oxy-fuel spraying, and plasma spraying. The following is a brief summary of the basic components and functioning of one type of each of the above mentioned thermal spray processes of the invention.

In cold spray thermal processing, generally powder particles are introduced into a high pressure gas where both the gas and particles enter a supersonic jet. The jet stream is directed against a mandrel in order to coat the mandrel with particles and form either tube stock or a coating. The cold spray process involves minimal heat input to the feedstock powder or the substrate thus making it possible to deposit thermally sensitive as well as conventional materials. The process generally produces high density, low residual stress deposits with low oxide contents.

The combustion wire thermal spray process is basically the spraying of molten metal onto a surface to provide tube stock or a coating. Material in wire form is melted in a flame (oxyacetylene flame is the most common) and atomized using compressed air to form a fine spray. When the spray contacts the prepared surface of a substrate material, the fine molten droplets rapidly solidify forming tube stock or a coating. This process carried out correctly is called a "cold process" (relative to the substrate material being coated) as the substrate temperature can be kept low during processing thereby avoiding damage, metallurgical changes and distortion to the substrate material.

The combustion powder thermal spray process is also basically the spraying of molten material onto a surface to provide tube stock or a coating. Here though, material in powder form is melted in a flame (oxy-acetylene or hydrogen is the most common) to form a fine spray. When the spray contacts the prepared surface of a substrate material, the fine molten droplets rapidly solidify forming tube stock or a coating. This process carried out correctly is called a "cold process" (relative to the substrate material being coated) as the substrate temperature can be kept low during processing thus avoiding damage, metallurgical changes and distortion to the substrate material.

In combustion wire spray processing, a wide range of material may be easily processed into powder form, giving a large choice of materials to use in making tube stock and/or coating devices. The process is limited only by materials with higher melting temperatures than the flame can provide or if the material decomposes on heating. In both, benefits include low capital investment, simplicity of operation, and high deposit efficiency.

In the arc spray process a pair of electrically conductive wires are melted by means of an electric arc. The molten material is atomized by compressed air and propelled towards the substrate surface. The impacting molten particles on the substrate rapidly solidify to form tube stock or a coating. This process carried out correctly is called a "cold process" (relative to the substrate material being coated) as the substrate temperature can be kept low during processing avoiding damage, metallurgical changes and distortion to the substrate material. Benefits of arc spray substrates and coatings includes high bond strength and density, low internal stresses, high thickness capability, and high quality microstructures.

The hvof (high velocity oxygen fuel) thermal spray process is similar to the combustion powder spray process except that hvof has been developed to produce extremely high spray velocity. Several hvof guns use different methods to achieve high velocity spraying. One method is basically a high pressure water cooled combustion chamber and long nozzle. Fuel (kerosene, acetylene, propylene and hydrogen) and oxygen are fed into the chamber, combustion produces a hot high pressure flame which is forced down a nozzle increasing its velocity. Powder may be fed axially into the combustion chamber under high pressure or fed through the side of laval type nozzle where the pressure is lower. Another method uses a simpler system of a high pressure combustion nozzle and air cap. Fuel gas (propane, propylene or hydrogen) and oxygen are supplied at high pressure, combustion occurs outside the nozzle but within an air cap supplied with compressed air. The compressed air pinches and accelerates the flame and acts as a coolant for the gun. Powder is fed at high pressure axially from the center of the nozzle. Benefits include high particle velocity, low particle temperatures, and time at temperature during the spraying process, which reduces oxidation and degradation of constituents.

The plasma spray process is basically the spraying of molten or heat softened material onto a surface to provide tube stock or a coating. Material in the form of powder is injected into a very high temperature plasma flame, where it is rapidly heated and accelerated to a high velocity. The hot material impacts on the substrate surface and rapidly cools forming tube stock or a coating. This process carried out correctly is called a "cold process" (relative to the substrate material being coated) as the substrate temperature can be kept low during processing thus avoiding damage, metallurgical changes and distortion to the substrate material.

The plasma gun comprises a copper anode and tungsten cathode, both of which are water cooled. Plasma gas (argon, nitrogen, hydrogen, helium) flows around the cathode and through the anode which is shaped as a constricting nozzle. The plasma is initiated by a high voltage discharge which causes localized ionization and a conductive path for a DC arc to form between cathode and anode. The resistance heating from the arc causes the gas to reach extreme temperatures, dissociate and ionize to form a plasma. The plasma exits the anode nozzle as a free or neutral plasma flame (plasma which does not carry electric current). When the plasma is stabilized and ready for spraying, the electric arc extends down the nozzle, instead of shorting out to the nearest edge of the anode nozzle. This stretching of the arc is due to a thermal pinch effect. Cold gas around the surface of the water cooled anode nozzle, being electrically non-conductive, constricts the plasma arc, raising its temperature and velocity. Powder is fed into the plasma flame most commonly via an external powder port mounted near the anode nozzle exit. The powder is so rapidly heated and accelerated that spray distances can be on the order of 25 to 150 mm. Benefits associated with plasma spray include a high degree of flexibility, the largest choice of substrate and coating materials, and high production spray rates in which the process can be highly automated.

The detonation gun basically consists of a long water cooled barrel with inlet valves for gases and powder. Oxygen and fuel (acetylene is the most common) is fed into the barrel along with a charge of powder. A spark is used to ignite the gas mixture and the resulting detonation heats and accelerates the powder to supersonic velocity down the barrel. A pulse of nitrogen is used to purge the barrel after each detonation. This process is repeated many times a second. The high kinetic energy of the hot powder particles on impact with the substrate result in a build up of a very dense and strong tube stock or coating.

The foregoing TSP processes provide a tubing product that can be formed into a stent that has strut cross-sections having an average grain size of less than or equal to 10 microns or an average thickness of about eight or more grains depending on the strut thickness. As stated, the disclosed processes also are applicable to the medical devices described herein.

Other features and advantages of the invention will become apparent from the following detailed description, taken in conjunction with the accompanying drawings, which illustrate, by way of example, the features of the invention.

DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within an artery.

FIG. 3 is an elevational view, partially in section showing the expanded stent within the artery after withdrawal of the delivery catheter.

DETAILED DESCRIPTION OF THE PREFERRED EMBODIMENTS

Figure 4:
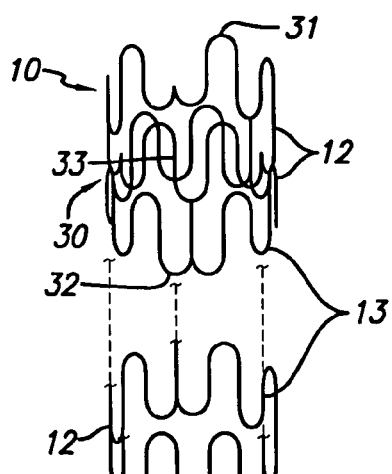
FIG. 4 is a perspective view of a stent embodying in an unexpanded state, with one end of the stent being shown in an exploded view to illustrate the details thereof.

The present invention relates to manufacturing processes for forming a medical device such as tube stock or piece of tubing, a wire, or to provide a coating on a tube for subsequent use as an intravascular stent, a guide wire, a ring marker, defibrillator lead tips, catheters and delivery systems. While virtually any medical device that is implanted or used in the body will benefit from the present invention, the invention as applied to stents is described herein as only an example and is not meant to be limiting. Thus, tube stock or wires made or coated by the process of the present invention might be used for stents, guide wires, catheters, markers, lead tips, and the like.

Stents are well known in the art and can have many different types of patterns and configurations. The following description of an intravascular stent as shown in FIGS. 1–5A, is a typical stent pattern made from stainless steel tubing. Other patterns are well known in the art and the foregoing description of a stent and delivery system is by way of example, and is not meant to be limiting.

Referring now to the drawings, and particularly FIG. 1 thereof, there is shown a stent 10 mounted onto a delivery catheter 11. The stent is a high precision patterned tubular device that typically includes a number of radially expandable cylindrical elements or rings 12 disposed generally coaxially and interconnected by links 13 disposed between adjacent rings. The delivery catheter has an expandable portion or balloon 14 for expanding the stent within an artery 15.

The typical delivery catheter 11 onto which the stent 10 is mounted is similar in operation to a conventional balloon dilatation catheter for angioplasty procedures. Portions of the proximal end of such catheters can be made of metal tubing or metal wire. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent to remain in place on the balloon during delivery to the site of the damage within the artery 15, the stent is compressed onto the balloon.

The delivery of the stent 10 is accomplished in the following manner. The stent is first mounted onto the inflatable balloon 14 on the distal extremity of the delivery catheter 11. The catheter-stent assembly is introduced within the patient's vasculature in a conventional Seldinger technique through a guiding catheter (not shown). A guide wire 18 is disposed across the damaged arterial section and then the catheter/stent assembly is advanced over the guide wire within the artery until the stent is directly within the target site. As stated, guide wires also will benefit from the processes of the present invention. The balloon of the catheter is expanded, expanding the stent against the artery, which is illustrated in FIG. 2. While not shown in the drawing, the artery is preferably expanded slightly by the expansion of the stent to seat or otherwise fix the stent to prevent movement. In some circumstances, during the treatment of stenotic portions of an artery, the artery may have to be expanded considerably in order to facilitate passage of blood or other fluid therethrough.

The stent 10 serves to hold open the artery 15 after the balloon 14 is deflated and the catheter 11 is withdrawn, as illustrated by FIG. 3. Due to the formation of the stent from an elongated tubular member, the undulating component of the rings 12 of the stent is relatively flat in transverse cross-section, so that when the stent is expanded, the rings are pressed into the wall of the artery and, as a result, do not interfere with the blood flow through the artery. Furthermore, the closely spaced rings at regular intervals provide uniform support for the wall of the artery and, consequently, are well adapted to hold open the artery, as illustrated in FIGS. 2 and 3.

FIG. 4 is an enlarged perspective view of the stent 10 shown in FIG. 1 with one end of the stent shown in an exploded view to illustrate in greater detail the placement of links 13 between adjacent radially expandable rings. In the embodiment shown in FIG. 4, the stent has three links between adjacent radially expandable rings that are approximately 120° apart. Each pair of links on one side of a ring are circumferentially offset 60° from the pair on the other side of the ring. The alternation of the links results in a stent which is longitudinally flexible in essentially all directions.

Figure 5:
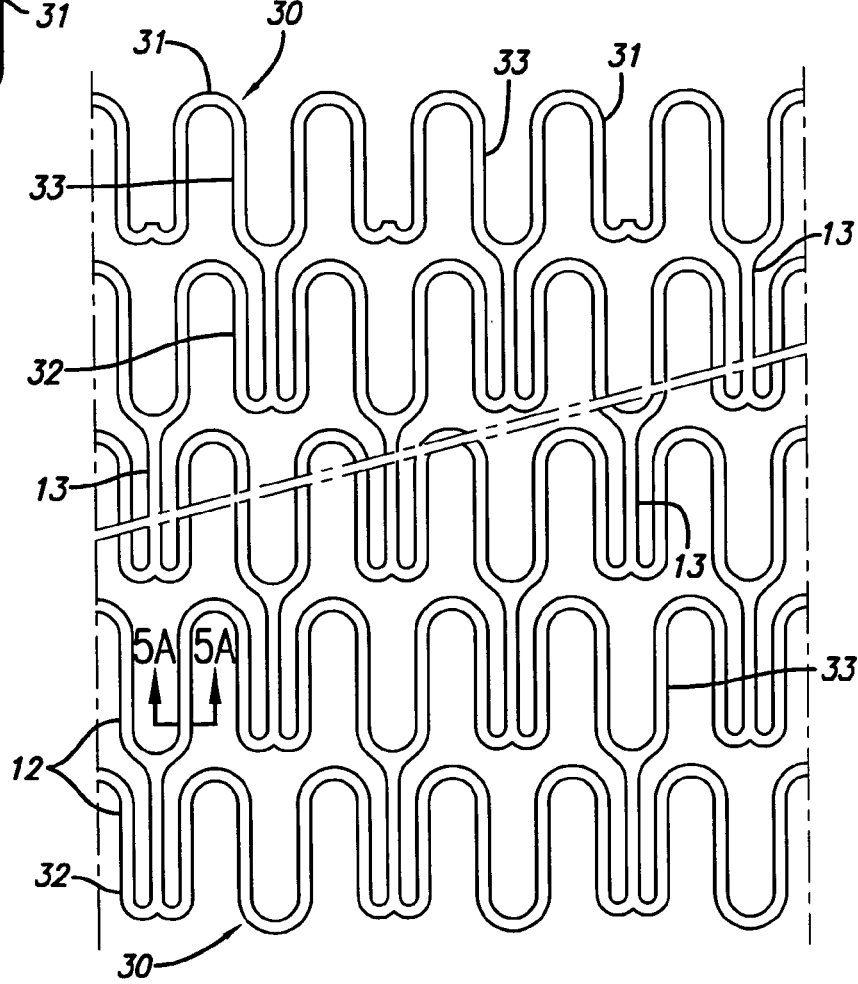
FIG. 5 is a plan view of a flattened section of a stent of the invention which illustrates the undulating pattern of the stent shown in FIG. 4.
Figure 5A:
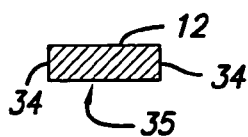
FIG. 5A is a cross-sectional view taken along the line 5A—5A in FIG. 5.

As best observed in FIGS. 4 and 5, the rings 12 are in the form of a serpentine pattern 30. As previously mentioned, each ring is connected by links 13. The serpentine pattern is made up of a plurality of U-shaped members 31, W-shaped members 32, and Y-shaped members 33, each having a different radius so that expansion forces are more evenly distributed over the various members. Other stent patterns can be formed by utilizing the processes of the present invention and the embodiment illustrated in FIGS. 1–5 are by way of example and are not intended to be limiting.

The aforedescribed illustrative stent 10 and similar stent structures can be made in many ways. The preferred method of making the disclosed stent in this invention is through a process utilizing thermal spray processing.

For use in coronary arteries, the stent diameter is very small, so the tubing from which it is made must necessarily also have a small diameter. Typically, the stent has an outer diameter on the order of about 0.030 to 0.060 inch in the unexpanded condition, equivalent to the tubing from which the stent is made, and can be expanded to an outer diameter of 0.10 inch or more. The wall thickness of the tubing is about 0.0020 to 0.010 inch. As with the foregoing stent dimensions, all of the medical devices that can be formed utilizing the present invention can vary substantially in size and shape so that the disclosed dimensions and shapes are representative examples only and are not meant to be limiting.

In its most basic form, the process of manufacturing tube stock or a coating in this invention consists of first selecting a thermal spray processing apparatus from the group consisting cold spray, combustion, hvof, arc, and plasma. Material selected from the group consisting of metals, alloys, polymers, ceramics, and cermets is then thermally spray formed onto either a mandrel to form tube stock or a stent to form a coating. Finally, the tube stock or coated stent is removed for further processing.

Figure 6:
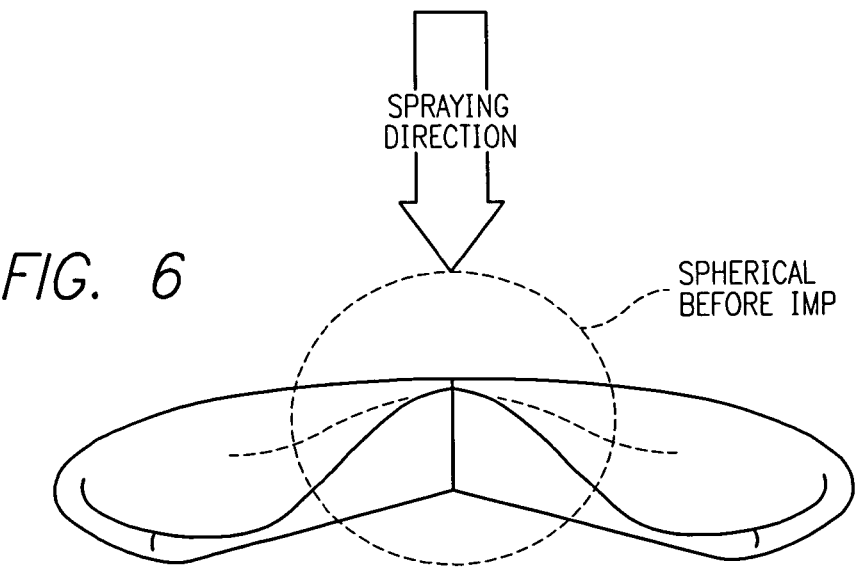
FIG. 6 is a schematic diagram of a spherical particle impinged onto a flat substrate (splat).
Figure 7:
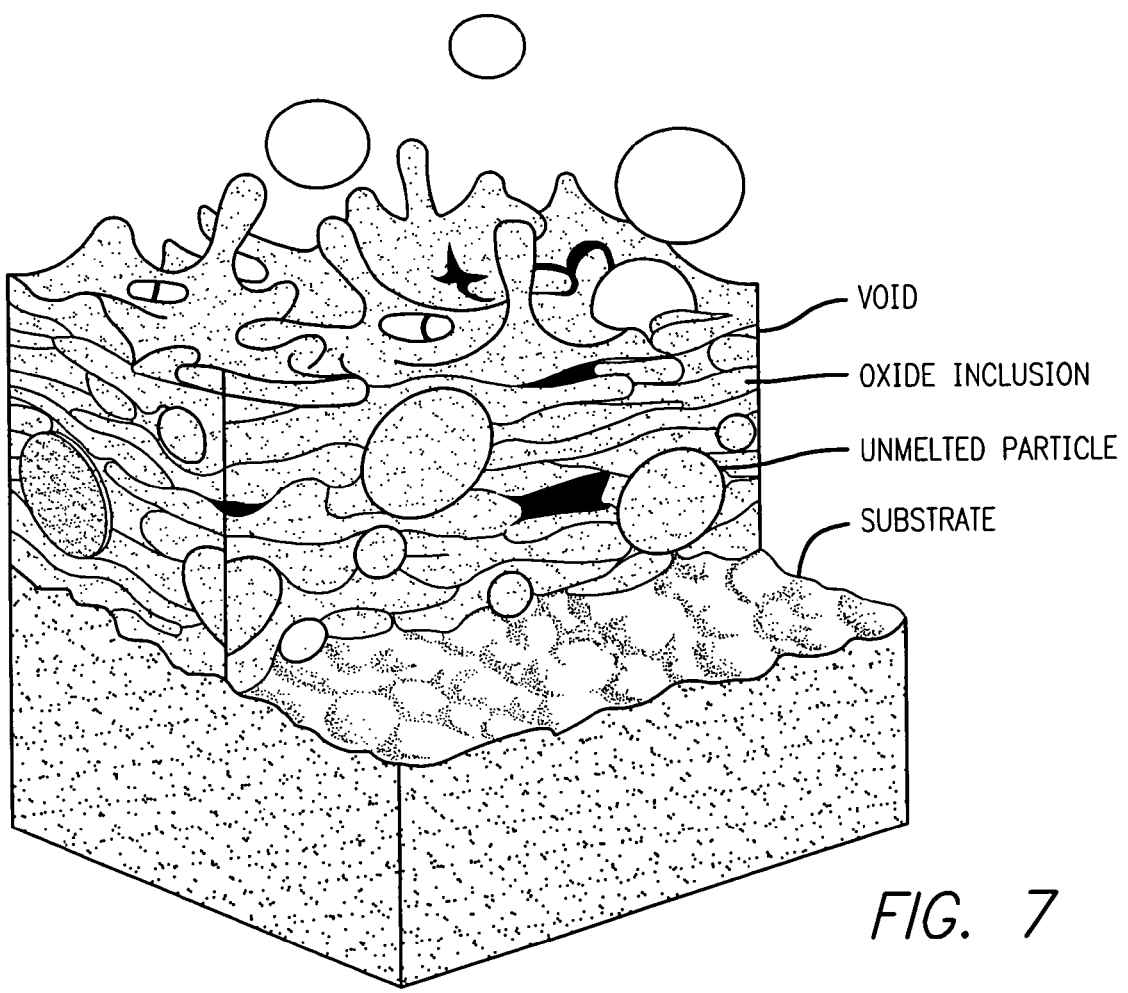
FIG. 7 is a schematic diagram of a thermal spray coating.

Thermal spray deposits are generally composed of cohesively bonded splats as shown in FIGS. 6 and 7 resulting from the impact, spreading, and rapid solidification of a high flux of particles with deformed shapes. The physical properties and behavior of the deposit depend on many factors including the cohesive strength among the splats, the size and morphology of the porosity, and the occurrence of cracks and defects and on the ultrafine-grained microstructure within the splats themselves.

The cold spray method offers a means for expanding the operational window for coating and forming stents to permit a variety of materials to be deposited with much lower thermal exposure than encountered in the traditional processes. The method exploits properties of gas dynamics which permit supersonic gas streams and attendant particle velocities to be obtained. The method additionally permits a high degree of spatial control by virtue of the gas nozzle characteristics and generally short standoff distances which can be employed. This results in a uniform structure of the coating or tube stock with the substantially preserved formation of the powder material without phase transformations and hardening, i.e., the coatings applied do not crack, their corrosion resistance, microhardness, and cohesion and adhesion strength are enhanced. The process includes producing a coating having an average grain size of between 1 and 64 microns and providing a thin walled structure having a wall thickness of about eight or more grains. While the grain size for thin walled structures (such as stents) has been referred to herein as about eight or more grains, the number of grains does vary depending on wall thickness. Thus, for very thin walled structures the wall thickness may be between four and eight grains, but for most (but not all) stent applications it is desirable to have at least eight or more grains comprising the wall thickness.

Typical values for tensile adhesion of the cold spray coatings are in the range of 30–801 MPa (4.4–11.6 ksi), with porosities in the range of 1–10 volume percent, deposit thicknesses ranging from 10 microns to 10 millimeters, deposition rates in the range of 0.010 to about 0.080 m$^3$ per hour, and deposition efficiencies in the range of 50–80%. Several considerations are the dependency of porosity on the ambient spray environment, powder characteristics (i.e., particle size and size distribution), and thermal-spray parameters (e.g., powder level, gas-flow features, and spray distance). The spray environment will have a significant influence on, for example, oxidation of metals, leading to greater porosity.

Figure 8:
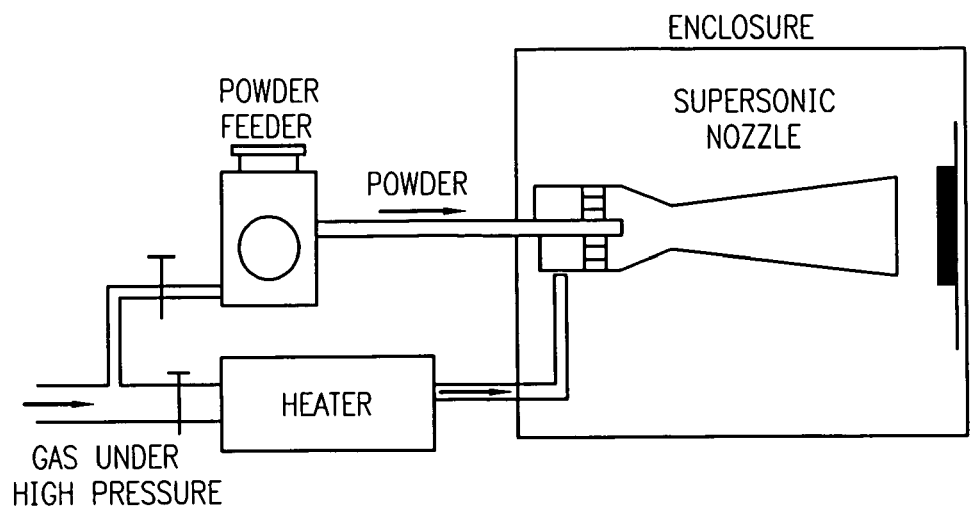
FIG. 8 is a schematic diagram of a cold spray thermal spray processing apparatus.

One embodiment utilizes cold spray thermal processing to manufacture the tube stock and apply coatings as shown in FIG. 8. In this process, particles of a powder of at least one first material are selected from the group including metals, metal alloys, or polymers and mechanical mixture of a metal and an alloy. The preferred particle size ranges from about 1 to 64 microns. The powder is fed through the powder feeder and then introduced into a gas selected from the group of Nitrogen ($N_2$), Oxygen ($O_2$), Air, Helium (He), Argon (Ar), Xenon (Xe), or Carbon Dioxide ($CO_2$). The gas also passes through the heater. Both the gas and particles are then fed into the supersonic nozzle with an inlet temperature between about 380 to 420° Celsius. The corresponding inlet velocity ranges from about 300 to about 1,200 m/sec and the inlet pressure is preferred to be between 1.5 to 2.5 Mpa. The nozzle is then directed against a mandrel which is placed 8 to 10 mm away. The mandrel is thereafter coated with the particles to form the tube stock or coating desired. Finally, the tube stock or coated stent is removed from the mandrel after it is formed.

Figure 9:
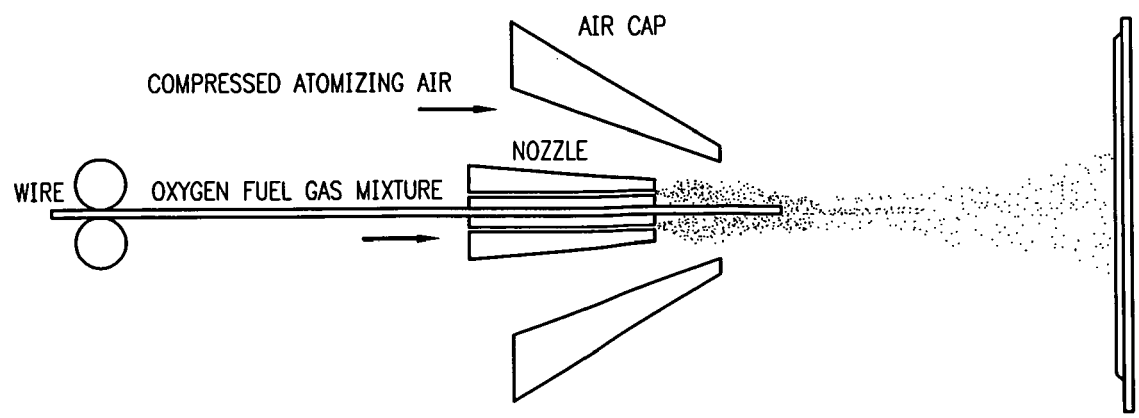
FIG. 9 is a schematic diagram of a combustion wire thermal spray processing apparatus.

The combustion wire thermal spray process shown in FIG. 9 is basically the spraying of molten particles onto a mandrel to produce tube stock or a coating. The wire is propelled and melted into the flame (oxy-acetylene flame most common) and atomized by the compressed air to form a fine spray. When the spray contacts the prepared surface, the fine molten droplets rapidly solidify forming tube stock or a coating. This process, carried out correctly, is called a "cold process" (relative to the substrate material being coated) as the substrate temperature can be kept low during processing thus avoiding damage, metallurgical changes and distortion to the substrate material.

Figure 10:
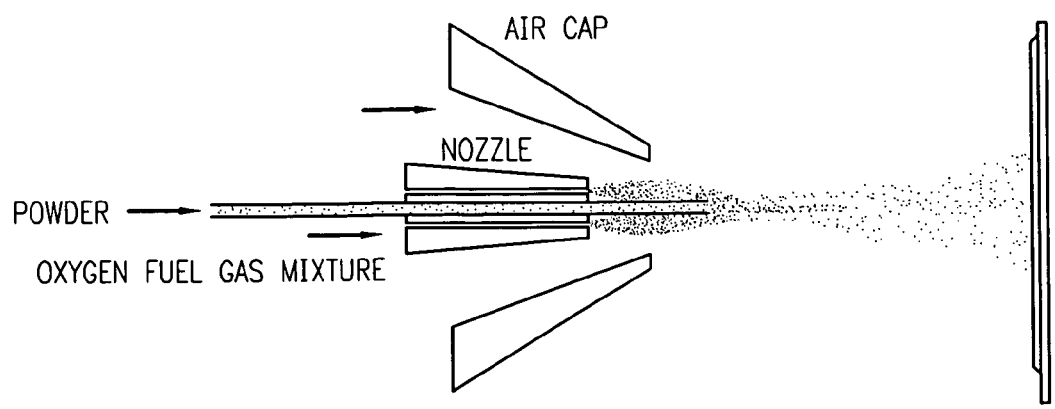
FIG. 10 is a schematic diagram of a combustion powder thermal spray processing apparatus.

The combustion powder thermal spray process shown in FIG. 10 is also basically the spraying of molten material onto a surface to provide tube stock or a coating. Here though, powder is propelled and melted into the flame (oxy-acetylene or hydrogen most common) to form a fine spray. When the spray contacts the prepared surface, the fine molten droplets rapidly solidify forming tube stock or a coating. This process, carried out correctly, is also called a "cold process" (relative to the substrate material being coated) as the substrate temperature can be kept low during processing thus avoiding damage, metallurgical changes and distortion to the substrate material.

In combustion wire spray processing there is a wide range of materials that can be easily processed into powder form giving a larger choice of coatings. The process is only limited by materials with higher melting temperatures than the flame can provide or if the material decomposes on heating.

Figure 11:
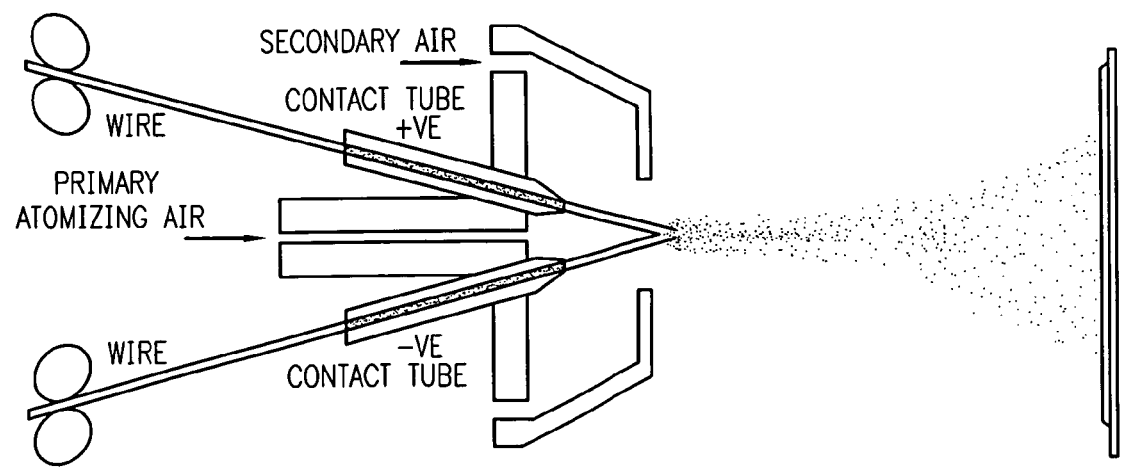
FIG. 11 is a schematic diagram of an arc wire thermal spray processing apparatus.

In the arc spray process shown in FIG. 11, a pair of electrically conductive wires are melted by means of an electric arc created between the two. The molten material is atomized by the compressed air and propelled towards the substrate surface. The impacting molten particles on the substrate rapidly solidify to form tube stock or a coating. This process, carried out correctly, is called a "cold process" (relative to the substrate material being coated) as the substrate temperature can be kept low during processing thus avoiding damage, metallurgical changes and distortion to the substrate material.

Figure 12:
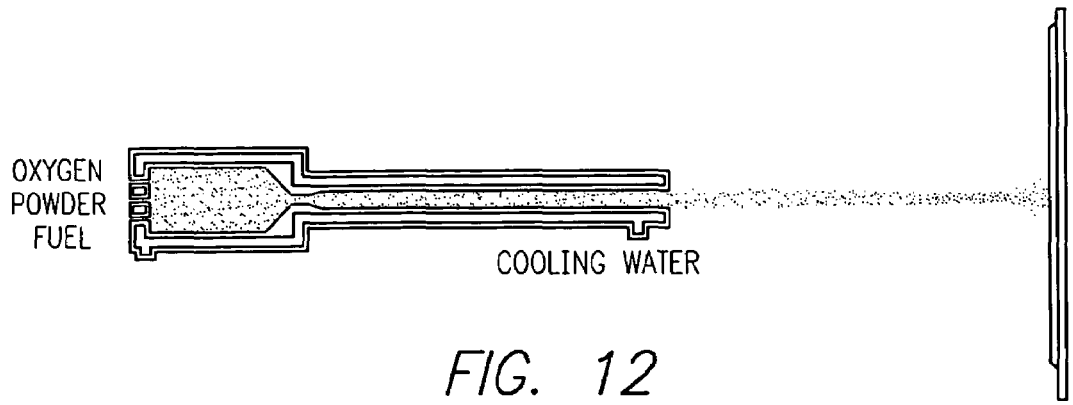
FIG. 12 is a schematic diagram of an hvof thermal spray processing apparatus.

The hvof (high velocity oxygen fuel) thermal spray process shown in FIG. 12 is similar to the combustion powder spray process except that hvof has been developed to produce extremely high spray velocities. There are a number of hvof guns which use different methods to achieve high velocity spraying. The method shown is basically a high pressure water cooled combustion chamber and long nozzle. Fuel (kerosene, acetylene, propylene and hydrogen) and oxygen are fed into the chamber where combustion produces a hot high pressure flame which is forced down a nozzle thereby increasing its velocity. The powder may be fed axially into the combustion chamber under high pressure or fed through the side of laval type nozzle where the pressure is lower. Another method (not shown here) uses a simpler system of a high pressure combustion nozzle and air cap. Fuel gas (propane, propylene or hydrogen) and oxygen are supplied at high pressure, combustion occurs outside the nozzle but within an air cap supplied with compressed air. The compressed air pinches and accelerates the flame and acts as a coolant for the gun. Powder is fed at high pressure axially from the center of the nozzle. The gas and particle velocity exiting an hvof gun can be in excess of 2500 feet per second. The velocity of the metallic particles causes friction through kinetic energy when the particles make contact with a substrate. This high energy can aid in the melting and adhesion of the particles to the substrate. Further, the gas temperature is usually very high, ranging from 2500° to 4500° F.

Figure 13:
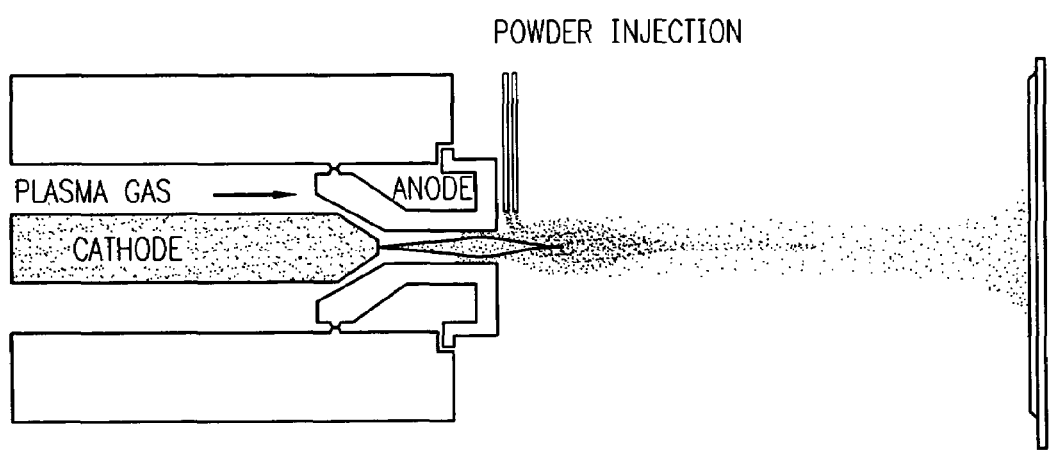
FIG. 13 is a schematic diagram of a plasma thermal spray processing apparatus.

The plasma spray process shown in FIG. 13 is basically the spraying of molten or heat softened material onto a surface to provide tube stock or a coating. Powdered material is directed through the powder injection and into the high temperature plasma flame, where it is rapidly heated and accelerated to a high velocity. The hot material impacts on the substrate surface and rapidly cools forming tube stock or a coating. This process is called a "cold process" (relative to the substrate material being coated) as the substrate temperature can be kept low during processing to avoid damage, metallurgical changes and distortion to the substrate material.

The plasma gun described above comprises a copper anode and tungsten cathode, both of which are water cooled. Plasma gas (argon, nitrogen, hydrogen, helium) flows around the cathode and through the anode which is shaped as a constricting nozzle. The plasma is initiated by a high voltage discharge which causes localized ionization and a conductive path for a DC arc to form between cathode and anode. The resistance heating from the arc causes the gas to reach extreme temperatures, dissociate and ionize to form a plasma. The plasma exits the anode nozzle as a free or neutral plasma flame (plasma which does not carry electric current). When the plasma is stabilized and ready for spraying, the electric arc extends down the nozzle, instead of shorting out to the nearest edge of the anode nozzle. This stretching of the arc is due to a thermal pinch effect. Due to the tremendous heat, the plasma gun components must be constantly cooled with water to prevent the gun from melting down. Water is sent to the gun through the same lines as electrical power. Small temperature changes in the cooling water may affect the ability to produce high quality plasma coatings. Therefore, a water chiller can be used to help produce high quality tube stock and coatings. Cold gas around the surface of the water cooled anode nozzle being electrically non-conductive constricts the plasma arc, raising its temperature and velocity. Powder is fed into the plasma flame most commonly via an external powder port mounted near the anode nozzle exit. The powder is so rapidly heated and accelerated that spray distances can be in the order of 25 to 150 mm. Typically, plasma begins generation at 10,000° F. Most plasma guns run between 15,000° F. and 30,000° F. internally.

Figure 14:
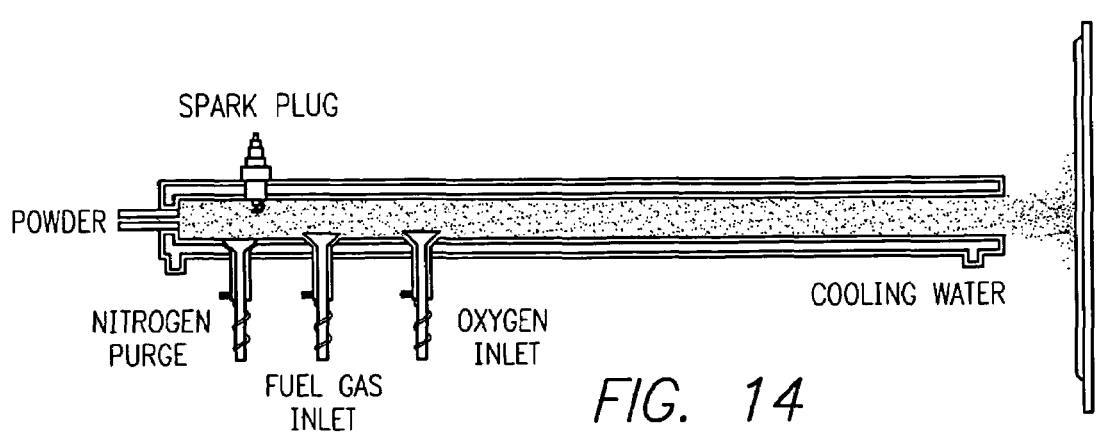
FIG. 14 is a schematic diagram of a detonation thermal spray processing apparatus.

The detonation gun shown in FIG. 14 basically consists of a long water cooled barrel with inlet valves for gases and powder. Oxygen and fuel (acetylene most common) are fed into the barrel along with a charge of powder. A spark from the spark plug is used to ignite the gas mixture and the resulting detonation heats and accelerates the powder to supersonic velocity down the barrel. A pulse of nitrogen is used to purge the barrel after each detonation. This process is repeated many times a second. The high kinetic energy of the hot powder particles on impact with the substrate result in a build up of a very dense and strong coating.

There are many possible variations on the above mentioned processes for forming tube stock or coating. Because the tube stock and coatings sought to be manufactured here are cylindrical, each of the above mentioned processes should incorporate either a moving thermal spray gun or a moving mandrel or substrate, or both, in order to uniformly disperse the material onto the mandrel to form tube stock or onto a stent to form a coating. This process is preferably accomplished through the use of a precision CNC machine.

For removal of the tube stock after it is formed, it may be beneficial to either melt or shrink the mandrel's diameter to ease removal of the tube stock. For example, the mandrel can be formed of metal that shrinks in diameter when cooled, while at the same time heating the tube stock so that it expands radially outwardly. The mandrel can then be easily removed from the tube stock. Also, the mandrel and tube stock may both be heated and the difference in expansion rates causing separation between the two. The mandrel can also be removed from the tube stock by a process called cross-rolling. The tube stock, with the mandrel inside, is run through a series of crossed rollers that will flex the tube stock and impart a separation between the tube and the mandrel, which is then easily removed. Alternatively, the mandrel could be lubricated so as to provide a low friction surface from which to slide the off tube stock.

Before the tube stock is removed from the mandrel one possibility for post processing, includes mechanically processing or swaging the tube stock in order to develop desired mechanical properties for subsequent use as a stent. After the tube stock is removed from the mandrel other post processing includes exerting high mechanical pressures onto the stent in order to develop the desired mechanical properties and tempering and hardening with a traveling ring furnace.

For correct sizing, the outer diameter and/or the inner diameter of the tube stock can be machined to size after being removed from the mandrel. The tube stock can also be reamed to size if desired. The tube stock can also be ground or drawn to final size.

As mentioned above, the invention also includes the process of coating a stent. The process includes thermally spray-forming material onto a stent pattern (see FIGS. 1–5) to form the coating where the type of thermal spray processing is selected from the group of cold spray, combustion, hvof, arc, and plasma. The material forming the coating is selected from the group of metals, metal alloys, polymers, ceramics, and cermets. As should be clear, other medical devices such as guide wires, lead tips, catheters, and markers also can be coated.

One modification after the coating is applied can include varying the radial thickness of the coating around the stent. In this process, the radial thickness can either be varied around the diameter or along the length of the stent. Further, the materials used to coat the stent can be varied. In one instance metallic alloys can be sprayed onto the stent while in others ceramics, polymers and composites can be sprayed on as coatings.

In one embodiment it may be desirable to spray a metallic coating onto the stent, heat the coating, and grow the grains after the coating is applied to the stent. In all instances, it may be possible to mechanically process or swage, anneal, heat treat, or cross link process the stent with the coating thereon in order to develop desired mechanical properties.

Additional post processing steps to reach the desired mechanical properties can include processing the stent in a traveling ring furnace where the material is melted and re-solidified as the ring travels down the length of the stent and processing the stent under high mechanical pressure in a vacuum to sinter grains of the stent together. To finish the coated stent to desired dimensions, the outer diameter of the stent can be post processed through centerless grinding or drawing to reduce the coating thickness. The inner diameter can be bored to improve both dimensions and surface roughness.

Figure 15:
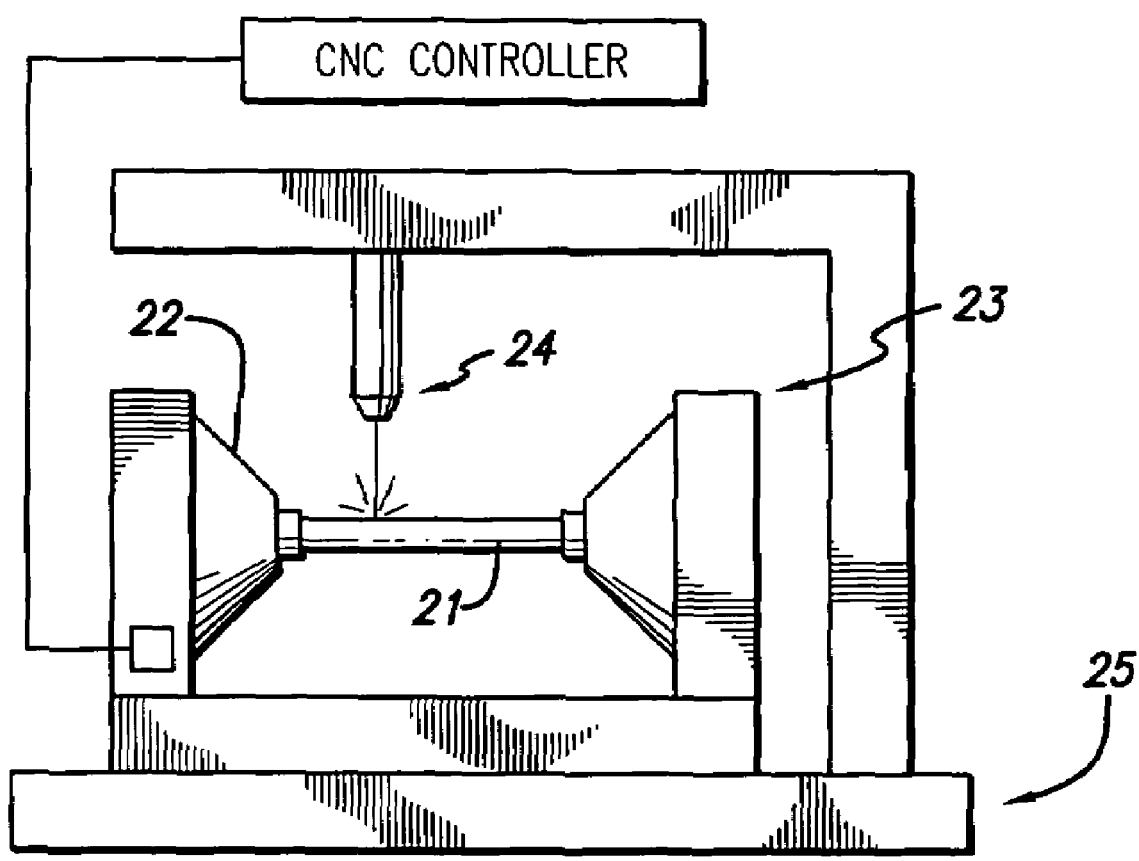
FIG. 15 is a schematic representation of equipment for selectively cutting the tubing in the manufacture of stents, in accordance with the present invention.

After thermal spray processing, it may be preferred to cut the tubing in the desired pattern by means of a machine-controlled laser as illustrated schematically in FIG. 15. A machine-controlled laser cutting system is generally depicted as disclosed in U.S. Pat. No. 5,780,807, which is commonly owned and commonly assigned to Advanced Cardiovascular Systems, Inc., Santa Clara, Calif., and which is incorporated herein by reference. The tubing 21 is placed in a rotatable collet fixture 22 of a machine-controlled apparatus 23 for positioning the tubing relative to the laser 24. According to machine-encoded instructions the tubing is rotated and moved longitudinally relative to the laser, which is also machine-controlled. The laser selectively removes the material from the tubing by ablation and a pattern is cut into the tube. The tube is therefore cut into the discrete pattern of the finished stent.

While several particular forms of the invention have been illustrated and described, it will also be apparent that various modifications can be made without departing from the scope of the invention.

What is claimed:

1. A method of coating a medical device, comprising:
   providing a medical device;
   providing a coating material containing a metal alloy; and
   applying the coating material to the medical device by cold spray thermal processing wherein powder particles are introduced into a high pressure gas where both the gas and particles enter a supersonic jet which is directed against the medical device, wherein the thickness of the coating containing a metal alloy is varied around the diameter or along the length of the medical device and wherein the medical device is selected from the group consisting of a stent, guide wires, lead tips, catheters and markers.

2. The method of claim 1, further comprising varying the thickness of the metal alloy coating along a length of the medical device.

3. The method of claim 1, wherein providing the medical device comprises forming the medical device into a stent.

4. The method of claim 1, wherein the coating material further comprises ceramic material.

5. The method of claim 1, wherein the coating material comprises a composite material.

6. The method of claim 1, wherein polymers are coated onto the medical device.

7. The method of claim 1, further comprising heat treating the coating formed from the thermal spray-forming of the metal alloy to grow the grain size of the coating.

8. The method of claim 1, further comprising swaging the medical device after thermally spray-forming material onto the medical device.

9. The method of claim 1, wherein the medical device is drawn after the coating is formed.

10. The method of claim 1, wherein the medical device is annealed after the coating is formed.

11. The method of claim 1, wherein the medical device is heated for post-processing after the coating is formed.

12. The method of claim 1, wherein after the coating is formed, the medical device is post processed in a traveling ring furnace where the material is melted and resolidified as the ring travels the length of the medical device.

13. The method of claim 1, further comprising processing the medical device in a vacuum and under high mechanical pressure so as to sinter the material forming the coating.

14. The method of claim 1, wherein after the coating is formed, an outer diameter of the medical device is post processed through centerless grinding.

15. The method of claim 1, wherein after the coating is formed, an outer diameter of the medical device is post processed by drawing to reduce the coating thickness.

16. The method of claim 1, wherein after the coating is formed, an inner diameter of the medical device is post processed by boring for improving both dimension and surface roughness.

* * * * *